(12) United States Patent
Wolff et al.

(10) Patent No.: US 7,179,303 B2
(45) Date of Patent: Feb. 20, 2007

(54) ACTIVE INGREDIENT COMBINATIONS FOR HAIR-DYEING AGENTS

(75) Inventors: Wolfgang Wolff, Bargteheide (DE); Mustafa Akram, Hamburg (DE); Hiroshi Tanaka, deceased, late of Urawa (JP); by Shigeri Tanaka, legal representative, Saitama (JP)

(73) Assignee: Henkel Kommanditgesellschaft Auf Aktien (Henkel KGaA), Duesseldorf (DE)

(*) Notice: Subject to any disclaimer, the term of this patent is extended or adjusted under 35 U.S.C. 154(b) by 0 days.

(21) Appl. No.: 10/691,427

(22) Filed: Oct. 22, 2003

(65) Prior Publication Data

US 2004/0133996 A1 Jul. 15, 2004

Related U.S. Application Data

(63) Continuation of application No. PCT/EP02/04275, filed on Apr. 18, 2002.

(30) Foreign Application Priority Data

Apr. 27, 2001 (DE) ................ 101 20 914

(51) Int. Cl.
*A61K 7/13* (2006.01)
(52) U.S. Cl. ............ 8/405; 8/406; 8/411; 8/455; 8/509; 8/516; 8/531; 8/540; 8/555; 8/558; 8/581
(58) Field of Classification Search ............ 8/405, 8/406, 411, 421, 455, 509, 516, 531, 540, 8/555, 558, 581
See application file for complete search history.

(56) References Cited

U.S. PATENT DOCUMENTS

| | | | |
|---|---|---|---|
| 4,003,699 A | 1/1977 | Rose et al. ............ 8/10.2 |
| 4,820,308 A | 4/1989 | Madrange et al. ........ 8/405 |
| 4,865,774 A | 9/1989 | Fabry et al. ............ 252/554 |
| 4,931,218 A | 6/1990 | Schenker et al. ........ 252/551 |
| 5,061,289 A | 10/1991 | Clausen et al. .......... 8/405 |
| 5,143,518 A * | 9/1992 | Madrange et al. ........ 8/405 |
| 5,294,726 A | 3/1994 | Behler et al. ............ 554/98 |
| 5,380,340 A | 1/1995 | Neunhoeffer et al. ..... 8/409 |
| 5,494,489 A | 2/1996 | Akram et al. ............ 8/408 |
| 5,534,267 A | 7/1996 | Neunhoeffer et al. ..... 424/70.1 |
| 5,663,366 A | 9/1997 | Neunhoeffer et al. ..... 548/371.4 |
| 5,735,908 A * | 4/1998 | Cotteret et al. ........ 8/410 |
| 5,766,576 A | 6/1998 | Lowe et al. ............ 424/62 |
| 6,099,592 A | 8/2000 | Vidal et al. ............ 8/409 |
| 6,162,424 A | 12/2000 | Decoster et al. ........ 424/70.17 |
| 6,270,533 B1 | 8/2001 | Genet et al. ............ 8/406 |
| 6,284,003 B1 | 9/2001 | Rose et al. ............ 8/412 |
| 6,306,181 B1 | 10/2001 | Terranova et al. ....... 8/409 |
| 6,312,677 B1 * | 11/2001 | Millequant et al. ...... 424/70.17 |
| 6,340,371 B1 | 1/2002 | Genet et al. ............ 8/406 |
| 6,379,398 B1 | 4/2002 | Genet et al. ............ 8/405 |
| 6,402,791 B1 | 6/2002 | Genet et al. ............ 8/405 |
| 6,419,711 B1 | 7/2002 | Genet et al. ............ 8/405 |
| 6,423,101 B1 | 7/2002 | Yaker et al. ............ 8/407 |
| 6,451,068 B1 | 9/2002 | Genet et al. ............ 8/405 |
| 6,455,737 B1 | 9/2002 | Vidal et al. ............ 564/305 |
| 6,461,389 B1 | 10/2002 | Genet et al. ............ 8/409 |
| 6,475,247 B1 | 11/2002 | Vandenbossche et al. .. 8/405 |
| 6,497,730 B1 | 12/2002 | Genet et al. ............ 8/405 |
| 6,537,329 B1 | 3/2003 | Vidal et al. ............ 8/405 |
| 6,544,298 B1 | 4/2003 | Vidal et al. ............ 8/405 |
| 6,565,614 B1 | 5/2003 | Genet et al. ............ 8/406 |
| 6,572,665 B2 | 6/2003 | Lim et al. .............. 8/405 |
| 6,605,124 B1 | 8/2003 | Vandenbossche et al. .. 564/305 |
| 2001/0023514 A1 * | 9/2001 | Cottard et al. .......... 8/406 |
| 2003/0131424 A1 | 7/2003 | Audousset ............. 8/405 |

FOREIGN PATENT DOCUMENTS

| | | |
|---|---|---|
| CA | 2 366 826 | 10/2000 |
| DE | 23 59 399 A1 | 6/1975 |
| DE | 37 23 354 A1 | 1/1989 |
| DE | 37 25 030 A1 | 2/1989 |

(Continued)

OTHER PUBLICATIONS

The Science of Hair Care, Chapter 7, pp. 246-259, published in vol. 7 Dermatology, Marcel Dekker Inc. NY/Basle (1986).

(Continued)

*Primary Examiner*—Eisa Elhilo
(74) *Attorney, Agent, or Firm*—John E. Drach; Stephen D. Harper

(57) ABSTRACT

A preparation for coloring keratin fibers containing dyes and/or dye precursors, at least one silicone oil and/or silicone gum and at least one polymer which contains at least one monomer unit corresponding to formula (I):

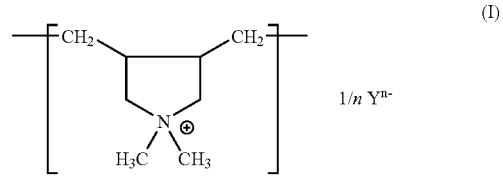

in which n is a number of 1 to 3 and Y is a physiologically compatible anion.

Also disclosed is a method of applying this preparation to keratin fibers.

14 Claims, No Drawings

FOREIGN PATENT DOCUMENTS

| | | |
|---|---|---|
| DE | 38 43 892 A1 | 6/1990 |
| DE | 39 26 344 A1 | 2/1991 |
| DE | 41 33 957 A1 | 4/1993 |
| DE | 44 08 506 A1 | 9/1995 |
| DE | 195 43 988 A1 | 5/1997 |
| DE | 199 14 926 A1 | 2/2000 |
| DE | 199 14 927 A1 | 10/2000 |
| EP | 0 740 931 A1 | 11/1996 |
| EP | 0 984 006 A1 | 3/2000 |
| EP | 0 984 007 A1 | 3/2000 |
| EP | 0 989 128 A1 | 3/2000 |
| EP | 1 224 927 A1 | 7/2002 |
| GB | 1026978 | 4/1966 |
| GB | 1153196 | 5/1969 |
| JP | 2-19576 | 1/1990 |
| JP | 5-194161 | 8/1993 |
| JP | 2002 179 538 A | 6/2002 |
| WO | WO 94/08969 A1 | 4/1994 |
| WO | WO 94/08970 A1 | 4/1994 |
| WO | WO 96/15765 A1 | 5/1996 |
| WO | WO 98/44897 A1 | 10/1998 |
| WO | WO 99/03819 A1 | 1/1999 |
| WO | WO 99/03834 A2 | 1/1999 |
| WO | WO 99/03836 A1 | 1/1999 |
| WO | WO 99/13845 A1 | 3/1999 |
| WO | WO 99/37278 A1 | 7/1999 |
| WO | WO 99/48856 A1 | 9/1999 |
| WO | WO 99/48874 A1 | 9/1999 |
| WO | WO 99/48875 A1 | 9/1999 |
| WO | WO 00/42971 A2 | 7/2000 |
| WO | WO 00/42979 A1 | 7/2000 |
| WO | WO 00/42980 A1 | 7/2000 |
| WO | WO 00/43356 A1 | 7/2000 |
| WO | WO 00/43368 A1 | 7/2000 |
| WO | WO 00/43386 A1 | 7/2000 |
| WO | WO 00/43388 A1 | 7/2000 |
| WO | WO 00/43389 A1 | 7/2000 |
| WO | WO 00/43396 A1 | 7/2000 |
| WO | WO 00/43967 A1 | 7/2000 |
| WO | WO 01/78669 A1 | 10/2001 |

OTHER PUBLICATIONS

The Science of Hair Care, Chapter 8, pp. 264-268, published in vol. 7 Dermatology, Marcel Dekker Inc. NY/Basle (1986).

K. Schrader, Grundlagen un Rezepturen der Kosmetika [Bases and Formulations Cosmetics], 2$^{nd}$ Edition, Huethig Buch Verlag, Heidelberg, Germany (1989).

* cited by examiner

ACTIVE INGREDIENT COMBINATIONS FOR HAIR-DYEING AGENTS

CROSS REFERENCE TO RELATED APPLICATIONS

This application is a continuation under 35 USC 365(c) and 35 USC 120 of international application PCT/EP02/04275, filed on Apr. 18, 2002, the international application not being published in English. This application also claims priority under 35 USC 119 to DE 101 209 14.2, filed on Apr. 27, 2001.

BACKGROUND OF THE INVENTION

This invention relates to hair colorants containing a combination of hair care ingredients and to a coloring process using this combination.

Nowadays, human hair is treated in many different ways with hair-care preparations. Such treatments include, for example, the cleaning of hair with shampoos, the care and regeneration of hair with rinses and treatments and the bleaching, coloring and shaping of hair with coloring and tinting formulations, wave formulations and styling preparations. Among these, formulations for modifying or shading the color of the hair occupy a prominent position.

So-called oxidation colorants are used for permanent, intensive colors with corresponding fastness properties. Oxidation colorants normally contain oxidation dye precursors, so-called primary intermediates and secondary intermediates. The primary intermediates form the actual dyes with one another or by coupling with one or more secondary intermediates under the influence of oxidizing agents or atmospheric oxygen. Combinations of oxidation dyes and substantive dyes are often also used to obtain special shades. Oxidation colorants are distinguished by excellent long-lasting coloring results.

Colorants or tints containing substantive dyes as their coloring component are normally used for temporary colors. Substantive dyes are based on dye molecules which are directly absorbed onto the hair and do not require an oxidative process for developing the color. Dyes such as these include, for example, henna which has been used since ancient times for coloring the body and hair. Corresponding colors are generally sensitive to shampooing so that an often unwanted change of shade or even a visible "decoloration" can occur.

A disadvantage of temporary colors of the type in question is that they are added onto the natural hair color and hence only allow shades that are darker than the starting color. Because of this, colorants based on substantive dyes are often used in combination with preparations of oxidizing agents in order to lighten the starting color of the fibers besides actually coloring them.

Accordingly, both processes necessitate the use of strong oxidizing agents, such as hydrogen peroxide solutions for example. This can damage the hair to be colored which then has to be treated with corresponding hair care products to counteract the damage.

It has therefore long been standard practice to subject the hair to a special aftertreatment. In this special aftertreatment, the hair is treated with special active substances, for example quaternary ammonium salts or special polymers, normally formulated as a rinse. Depending on the formulation, this treatment improves the combability, hold and volume of the hair and reduces the number of split ends.

In addition, so-called combination preparations have very recently been developed to reduce the effort involved in the usual multistep processes, particularly where they are directly applied by the user.

Besides the usual components, for example for coloring the hair, these preparations additionally contain active substances which, previously, had been reserved for the aftertreatment preparations. Accordingly, the user has one less step to carry out. At the same time, packaging costs are reduced because one product less is used.

The active substances used in such combination preparations have to meet stringent requirements, particularly in regard to their stability, because the coloring creams normally have a high pH and the oxidizing agent preparations a low pH. In addition, incompatibilities between the various active substances and hence poor stability in storage have to be avoided.

Patent applications DE-A-199 14 927, DE-A-199 14 926 and DE-A-44 08 506 disclose such combinations of active substances for use in oxidative colorants. Nevertheless, corresponding preparations are still unsatisfactory in regard to their hair care properties, particularly on hair that does not readily lend itself to care, such as Japanese hair for example.

Accordingly, there is a still a need for active substances or combinations of active substances which would couple good hair care properties with ready biodegradability and which would not have any tendency towards unwanted accumulation on the hair.

SUMMARY OF THE INVENTION

It has now surprisingly been found that a combination of silicone oils and special polymers does not have any of the above-mentioned disadvantages and, at the same time, improves the feel, wet combability and luster of the treated fibers, particularly in the case of Asiatic hair.

The preparations according to the invention are also distinguished by their ease of application, i.e. the preparations have a consistency which provides for good adhesion to the fibers and is not too thin. It has been found that the active-substance combination according to the invention also shows surprising synergism in regards to its thickening properties.

DETAILED DESCRIPTION OF THE INVENTION

In a first embodiment, therefore, the present invention relates to a preparation for coloring keratin fibers which, besides dyes and/or dye precursors, contains a combination of hair care components consisting of (A) at least one silicone oil and/or a silicone gum and
(B) at least one polymer containing at least one monomer unit corresponding to formula (I):

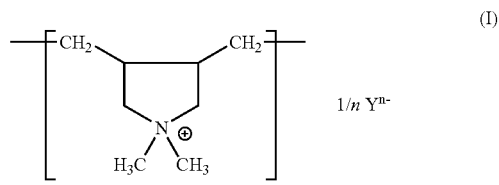

in which n is a number of 1 to 3 and Y is a physiologically compatible anion.

Keratin fibers in the context of the invention are understood to be pelts, wool, feathers and, in particular, human hair.

According to the invention, physiologically compatible anions are, for example, chloride, bromide, sulfate, phosphate, acetate, propionate, citrate and lactate. A preferred anion according to the invention is chloride.

Although, in a preferred embodiment of the invention, both components of the active substance combination are incorporated in the coloring cream, component (A) may even be present in the oxidizing agent preparation in another embodiment. In this embodiment, the preparation containing the active substance combination according to the invention is only obtained after mixing of the two components.

According to the invention, suitable silicones or silicone gums are, in particular, dialkyl and alkylaryl siloxanes such as, for example, dimethyl polyslioxane and methylphenyl polysiloxane and alkoxylated, quaternized and anionic derivatives thereof.

Examples of such silicones are:
oligomeric polydimethyl cyclosiloxanes (INCI name: Cyclomethicone), more particularly the tetrameric and the pentameric compounds which are marketed under the names of DC 344 and DC 345 by Dow Corning,
hexamethyl disiloxane (INCI name: Hexamethyldisiloxane), for example the product marketed under the name of Abil® K 520,
polymeric polydimethyl siloxanes (INCI name: Dimethicone), for example the products marketed under the name of DC 200 by Dow Corning,
polyphenyl methyl siloxanes (INCI name: Phenyl Trimethicone), for example the product marketed under the name of DC 566 Fluid by Dow Corning,
silicone/glycol copolymers (INCI name: Dimethicone Copolyol), for example the products marketed under the names of DC 190 and DC 193 by Dow Corning,
esters and partial esters of silicone/glycol copolymers which are marketed under the name of Fancorsil® LIM by Fanning (INCI name: Dimethicone Copolyol Meadowfoamate),
hydroxy-terminated dimethyl siloxanes (INCI name: Dimethiconol), for example the products DC 1401 and Q2-1403 marketed by Dow Corning,
aminofunctional polydimethylsiloxanes and hydroxylamino-modified silicones (INCI name: inter alia Amodimethicone and Quaternium-80), such as the commercial products XF42-B1989 (manufacturer: GE Toshiba Silicones), Q2-7224 (manufacturer: Dow Corning, a stabilized trimethylsilyl amodimethicone), Dow Corning® 939 Emulsion (containing a hydroxylamino-modified silicone which is also known as amodimethicone), SM-2059 (manufacturer: General Electric), SLM-55067 (manufacturer: Wacker) and Abil®-Quat 3270 and 3272 (manufacturer: Th. Goldschmidt),
anionic silicone oils such as, for example, the product Dow Corning® 1784.

In a preferred embodiment, the preparations according to the invention contain a combination of a volatile and a non-volatile silicone. Volatile silicones in the context of the invention are silicones which have a volatility equal to or higher than the volatility of the cyclic pentameric dimethyl siloxane. Such combinations are also obtainable as commercial products (for example Dow Corning® 1401, Dow Corning® 1403 and Dow Corning® 1501 which are each mixtures of a Cyclomethicone and a Dimethiconol).

In a particularly preferred embodiment, a dialkyl polysiloxane or one of its derivatives is used as component (A). The alkyl groups methyl, ethyl, i-propyl and n-propyl are preferred. Dimethyl polysiloxane or one of its derivatives is particularly preferred. The aminofunctional derivatives of dialkyl polysiloxane are preferred; the aminofunctional derivatives of dimethyl polysiloxane are particularly preferred. A most particularly preferred derivative is commercially available under the INCI name of Amodimethicone.

The preparations according to the invention contain the silicones in quantities of preferably 0.05 to 10% by weight and more particularly 0.1 to 5% by weight, based on the preparation as a whole.

In a first preferred embodiment, the components (B) of the combination of hair care ingredients according to the invention are cationic polymers. These are in particular the homopolymers of dimethyl diallyl ammonium salts (corresponding to the monomer units of formula (I)) and the copolymers of the dimethyl diallyl ammonium salts with esters and amides of acrylic acid and/or methacrylic acid. The products commercially available under the name of Merquat® 100 (poly(dimethyldiallylammonium chloride)) and Merquat® 550 (dimethyldiallyl ammonium chloride/acrylamide copolymer) are examples of such cationic polymers.

In a second preferred embodiment, the components (B) of the combination of hair care ingredients according to the invention are amphoteric polymers. These are in particular the copolymers of the dimethyldiallyl ammonium salts (corresponding to the monomer units of formula (I)) with acrylic acid and/or methacrylic acid. The copolymers with acrylic acid are particularly preferred. The product marketed under the name of Merquat® 280 (dimethyldiallyl ammonium chloride/acrylic acid copolymer, INCI name: Polyquaternium-22) is an example of such polymers.

Other particularly preferred amphoteric copolymers are those which, besides the monomer units of formula (I) and the acrylic acid and/or methacrylic acid units, contain at least one nonionic comonomer. Examples of such nonionic comonomers are the esters or amides of acrylic acid and/or methacrylic acid. The product marketed as Merquat® Plus 3330 (dimethyldiallyl ammonium chloride/acrylic acid/acrylamide terpolymer, INCI name: Polyquaternium-39) is an example of such a preferred polymer.

In a first preferred embodiment, the colorants according to the invention contain at least one dye precursor. The invention is not limited in any way in regard to the dye precursors used in the colorants according to the invention. The colorants according to the invention may contain
oxidation dye precursors of the primary and secondary intermediate type and
precursors of "nature-analogous" dyes, such as indole and indoline derivatives and mixtures of representatives of these groups as dye precursors.

The colorants according to the invention preferably contain at least one primary intermediate as dye precursor. The primary intermediates normally used are primary aromatic amines containing another free or substituted hydroxy or amino group in the para or ortho position, diaminopyridine derivatives, heterocyclic hydrazones, 4-aminopyrazole derivatives and 2,4,5,6-tetraamino pyrimidine and derivatives thereof.

In a particularly preferred embodiment of the invention, a p-phenylediamine derivative or one of its physiologically compatible salts is used as the primary intermediate. Partiular preference is attributed to p-phenylenediamine derivatives corresponding to formula (E1):

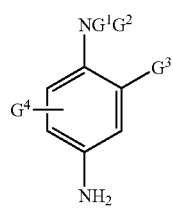

in which
- G¹ stands for a hydrogen atom, a $C_{1-4}$ alkyl radical, a $C_{1-4}$ monohydroxyalkyl radical, a $C_{2-4}$ polyhydroxyalkyl radical, a $(C_{1-4})$-alkoxy-$(C_{1-4})$-alkyl radical, a 4'-aminophenyl radical or a $C_{1-4}$ alkyl radical substituted by a nitrogen-containing group, a phenyl group or a 4'-aminophenyl group;
- G² stands for a hydrogen atom, a $C_{1-4}$ alkyl radical, a $C_{1-4}$ monohydroxyalkyl radical, a $C_{2-4}$ polyhydroxyalkyl radical, a $(C_{1-4})$-alkoxy-$(C_{1-4})$-alkyl radical or a $C_{1-4}$ alkyl radical substituted by a nitrogen-containing group;
- G³ stands for a hydrogen atom, a halogen atom, such as a chlorine, bromine, iodine or fluorine atom, a $C_{1-4}$ alkyl radical, a $C_{1-4}$ monohydroxyalkyl radical, a $C_{2-4}$ polyhydroxyalkyl radical, a $C_{1-4}$ hydroxyalkoxy radical, a $C_{1-4}$ acetylaminoalkoxy radical, a $C_{1-4}$ mesylaminoalkoxy radical or a $C_{1-4}$ carbamoylaminoalkoxy radical;
- G⁴ is a hydrogen atom, a halogen atom or a $C_{1-4}$ alkyl radical or
- if G³ and G⁴ are in the ortho position to one another, they may together form a bridging α,ω-alkylenedioxo group such as, for example, an ethylenedioxy group.

Examples of the $C_{1-4}$ alkyl radicals mentioned as substituents in the compounds according to the invention are the methyl, ethyl, propyl, isopropyl and butyl groups. Ethyl and methyl radicals are preferred alkyl radicals. According to the invention, preferred $C_{1-4}$ alkoxy radicals are, for example, methoxy or ethoxy radicals. Other preferred examples of a $C_{1-4}$ hydroxyalkyl group are the hydroxymethyl, 2-hydroxyethyl, 3-hydroxypropyl or 4-hydroxybutyl group. A 2-hydroxyethyl group is particularly preferred. According to the invention, examples of halogen atoms are F, Cl or Br atoms. Cl atoms are most particularly preferred. According to the invention, the other terms used are derived from the definitions given here. Examples of nitrogen-containing groups corresponding to formula (E1) are, in particular, the amino groups, $C_{1-4}$ monoalkylamino groups, $C_{1-4}$ dialkylamino groups, $C_{1-4}$ trialkylammonium groups, $C_{1-4}$ monohydroxyalkylamino groups, imidazolinium and ammonium.

Particularly preferred p-phenylenediamines corresponding to formula (E1) are selected from p-phenylenediamine, p-toluylenediamine, 2-chloro-p-phenylenediamine, 2,3-dimethyl-p-phenylenediamine, 2,6-dimethyl-p-phenylenediamine, 2,6-diethyl-p-phenylenediamine, 2,5-dimethyl-p-phenylenediamine, N,N-dimethyl-p-phenylenediamine, N,N-diethyl-p-phenylenediamine, N,N-dipropyl-p-phenylenediamine, 4-amino-3-methyl-(N,N-diethyl)-aniline, N,N-bis-(β-hydroxyethyl)-p-phenylenediamine, 4-N,N-bis-(β-hydroxyethyl)-amino-2-methylaniline, 4-N,N-bis-(β-hydroxyethyl)-amino-2-chloroaniline, 2-(β-hydroxyethyl)-p-phenylenediamine, 2-fluoro-p-phenylenediamine, 2-isopropyl-p-phenylenediamine, N-(β-hydroxypropyl)-p-phenylenediamine, 2-hydroxymethyl-p-phenylenediamine, N,N-dimethyl-3-methyl-p-phenylenediamine, N,N-(ethyl-β-hydroxyethyl)-p-phenylenediamine, N-(β,γ-dihydroxypropyl)-p-phenylenediamine, N-(4'-aminophenyl)-p-phenylenediamine, N-phenyl-p-phenylenediamine, 2-(β-hydroxyethyloxy)-p-phenylenediamine, 2-(β-acetylaminoethyloxy)-p-phenylenediamine, N-(β-methoxyethyl)-p-phenylenediamine and 5,8-diaminobenzo-1,4-dioxane and physiologically compatible salts thereof.

According to the invention, most particularly preferred p-phenylenediamine derivatives corresponding to formula (E1) are p-phenylenediamine, p-toluylenediamine, 2-(β-hydroxyethyl)-p-phenylenediamine and N,N-bis-(2-hydroxyethyl)-p-phenylenediamine.

In another preferred embodiment of the invention, compounds containing at least two aromatic nuclei substituted by amino and/or hydroxyl groups may be used as the primary intermediate.

The binuclear primary intermediates which may be used in the coloring compositions according to the invention include in particular compounds corresponding to formula (E2) and physiologically compatible salts thereof:

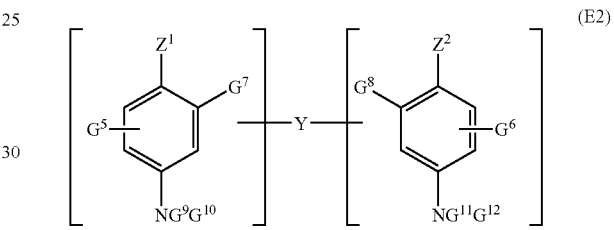

in which
- Z¹ and Z² independently of one another stand for a hydroxyl or $NH_2$ radical which is optionally substituted by a $C_{1-4}$ alkyl radical, by a $C_{1-4}$ hydroxyalkyl radical and/or by a bridging group Y or which is optionally part of a bridging ring system,
- the bridging group Y is a $C_{1-14}$ alkylene group such as, for example, a linear or branched alkylene chain or an alkylene ring which may be interrupted or terminated by one or more nitrogen-containing groups and/or one or more hetero atoms, such as oxygen, sulfur or nitrogen atoms, and may optionally be substituted by one or more hydroxyl or $C_{1-8}$ alkoxy radicals or a direct bond,
- G⁵ and G⁶ independently of one another stand for a hydrogen or halogen atom, a $C_{1-4}$ alkyl radical, a $C_{1-4}$ monohydroxyalkyl radical, a $C_{2-4}$ polyhydroxyalkyl radical, a $C_{1-4}$ aminoalkyl radical or a direct bond to the bridging group Y,
- G⁷, G⁸, G⁹, G¹⁰, G¹¹ and G¹² independently of one another stand for a hydrogen atom, a direct bond to the bridging group Y or a $C_{1-4}$ alkyl radical, with the provisos that
- the compounds of formula (E2) contain only one bridging group Y per molecule and
- the compounds of formula (E2) contain at least one amino group bearing at least one hydrogen atom.

According to the invention, the substituents used in formula (E2) are as defined in the foregoing.

Preferred binuclear primary intermediates corresponding to formula (E2) are, in particular, N,N'-bis-(β-hydroxyethyl)-N,N'-bis-(4'-aminophenyl)-1,3-diaminopropanol, N,N'-bis-(β-hydroxyethyl)-N,N'-bis-(4'-aminophenyl)-ethylenediamine, N,N'-bis-(4-aminophenyl)-tetramethylene diamine, N,N'-bis-(β-hydroxyethyl)-N,N'-bis-(4'-aminophenyl)-tetramethylene diamine, N,N'-bis-(4-methylaminophenyl)-tetramethylene diamine, N,N'-diethyl-N,N'-bis-(4'-amino-3'-methylphenyl)-ethylenediamine, bis-(2-hydroxy-5-aminophenyl)-methane, N,N'-bis-(4'-aminophenyl)-1,4-diazacycloheptane, N,N'-bis-(2-hydroxy-5-aminobenzyl)-piperazine, N-(4'-aminophenyl)-p-phenylenediamine and 1,10-bis-(2',5'-diaminophenyl)-1,4,7,10-tetraoxadecane and physiologically compatible salts thereof.

Most particularly preferred binuclear primary intermediates corresponding to formula (E2) are N,N'-bis-(β-hydroxyethyl)-N,N'-bis-(4'-aminophenyl)-1,3-diaminopropan-2-ol, bis-(2-hydroxy-5-aminophenyl)-methane, N,N'-bis-(4'-aminophenyl)-1,4-diazacycloheptane and 1,10-bis-(2',5'-diaminophenyl)-1,4,7,10-tetraoxadecane or a physiologically compatible salt thereof.

In another preferred embodiment of the invention, a p-aminophenol derivative or a physiologically compatible salt thereof is used as the primary intermediate. Particularly preferred p-aminophenol derivatives correspond to formula (E3):

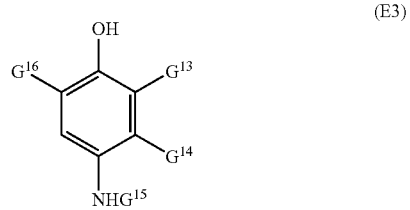

(E3)

in which
$G^{13}$ stands for a hydrogen atom, a halogen atom, a $C_{1-4}$ alkyl radical, a $C_{1-4}$ monohydroxyalkyl radical, a $C_{2-4}$ polyhydroxyalkyl radical, a $(C_{1-4})$-alkoxy-$(C_{1-4})$-alkyl radical, a $C_{1-4}$ aminoalkyl radical, a hydroxy-$(C_{1-4})$-alkylamino radical, a $C_{1-4}$ hydroxyalkoxy radical, a $C_{1-4}$ hydroxyalkyl-$(C_{1-4})$-aminoalkyl radical or a (di-$C_{1-4}$-alkylamino)-$(C_{1-4})$-alkyl radical, $G^{14}$ stands for a hydrogen atom or a halogen atom, a $C_{1-4}$ alkyl radical, a $C_{1-4}$ monohydroxyalkyl radical, a $C_{2-4}$ polyhydroxyalkyl radical, a $(C_{1-4})$-alkoxy-$(C_{1-4})$-alkyl radical, a $C_{1-4}$ aminoalkyl radical or a $C_{1-4}$ cyanoalkyl radical, $G^{15}$ stands for hydrogen, a $C_{1-4}$ alkyl radical, a $C_{1-4}$ monohydroxyalkyl radical, a $C_{2-4}$ polyhydroxyalkyl radical, a phenyl radical or a benzyl radical and $G^{16}$ stands for hydrogen or a halogen atom.

According to the invention, the substituents used in formula (E3) are defined as in the foregoing.

Preferred p-aminophenols corresponding to formula (E3) are, in particular, p-aminophenol, N-methyl-p-aminophenol, 4-amino-3-methylphenol, 4-amino-3-fluorophenol, 2-hydroxymethylamino-4-aminophenol, 4-amino-3-hydroxymethylphenol, 4-amino-2-(β-hydroxyethoxy)-phenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)-phenol, 4-amino-2-fluorophenol, 4-amino-2-chlorophenol, 4-amino-2,6-dichlorophenol, 4-amino-2-((diethylamino)methyl)phenol and physiologically compatible salts thereof.

Most particularly preferred compounds corresponding to formula (E3) are p-aminophenol, 4-amino-3-methylphenol, 4-amino-2-aminomethylphenol and 4-amino-2-(diethylaminomethyl)phenol.

In addition, the primary intermediate may be selected from o-aminophenol and its derivatives such as, for example, 2-amino-4-methylphenol, 2-amino-5-methylphenol or 2-amino-4-chlorophenol.

The primary intermediate may also be selected from heterocyclic primary intermediates such as, for example, pyridine, pyrimidine, pyrazole, pyrazole-pyrimidine derivatives and physiologically compatible salts thereof.

Preferred pyridine derivatives are, in particular, the compounds described in GB 1,026,978 and GB 1,153,196, such as 2,5-diaminopridine, 2-(4'-methoxyphenyl)-amino-3-aminopyridine, 2,3-diamino-6-methoxypyridine, 2-(β-methoxyethyl)-amino-3-amino-6-methoxypyridine and 3,4-diaminopyridine.

Preferred pyrimidine derivatives are, in particular, the compounds described in DE 2359399, JP 02019576 A2 and WO 96/15765, such as 2,4,5,6-tetraaminopyrimidine, 4-hydroxy-2,5,6-triaminopyrimidine, 2-hydroxy-4,5,6-triaminopyrimidine, 2-dimethylamino-4,5,6-triaminopyrimidine, 2,4-dihydroxy-5,6-diaminopyrimidine and 2,5,6-triaminopyridine.

Preferred pyrazole derivatives are, in particular, the compounds described in patents DE 3843892 and DE 4133957 and in patent applications WO 94/08969, WO 94/08970, EP 740931 and DE 19543988, such as 4,5-diamino-1-methylpyrazole, 4,5-diamino-1-(β-hydroxyethyl)-pyrazole, 3,4-diaminopyrazole, 4,5-diamino-1-(4'-chlorobenzyl)-pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methyl pyrazole, 4,5-diamino-3-tert.butyl-1-methylpyrazole, 4,5-diamino-1-tert.butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)-pyrazole, 4,5-diamino-1-ethyl-3-hydroxymethyl-pyrazole, 4,5-diamino-3-hydroxymethyl-1-methylpyrazole, 4,5-diamino-3-hydroxy-methyl-1-isopropylpyrazole, 4,5-diamino-3-methyl-1-isopropylpyrazole, 4-amino-5-(β-aminoethyl)-amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl)-amino-1-methylpyrazole.

Preferred pyrazole-pyrimidine derivatives are, in particular, the derivatives of pyrazole-[1,5-a]-pyrimidine corresponding to formula (E4) below and tautomeric forms thereof where a tautomeric equilibrium exists:

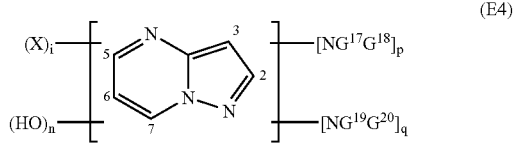

(E4)

in which
$G^{17}, G^{18}, G^{19}$ and $G^{20}$ independently of one another stand for a hydrogen atom, a $C_{1-4}$ alkyl radical, an aryl radical, a $C_{1-4}$ hydroxyalkyl radical, a $C_{2-4}$ polyhydroxyalkyl radical, a $(C_{1-4})$-alkoxy-$(C_{1-4})$-alkyl radical, a C$_{1-4}$ aminoalkyl radical which may optionally be protected by an acetylureide or sulfonyl radical, a (C$_{1-4}$)-alkylamino-(C$_{1-4}$)-alkyl radical, a di[(C$_{1-4}$)-alkyl]-(C$_{1-4}$)-aminoalkyl radical, the dialkyl radicals optionally forming a carbon cycle or a heterocycle with 5 or 6 links, a C$_{1-4}$ hydroxyalkyl or a di-(C$_{1-4}$)-[hydroxyalkyl]-(C$_{1-4}$)-aminoalkyl radical;

the X radicals independently of one another stand for a hydrogen atom, a C$_{1-4}$ alkyl radical, an aryl radical, a C$_{1-4}$ hydroxyalkyl radical, a C$_{2-4}$ polyhydroxyalkyl radical, a C$_{1-4}$ aminoalkyl radical, a (C$_{1-4}$)-alkylamino-(C$_{1-4}$)-alkyl radical, a di[(C$_{1-4}$)-alkyl]-(C$_{1-4}$)-aminoalkyl radical, the dialkyl radicals optionally forming a carbon cycle or a heterocycle with 5 or 6 links, a C$_{1-4}$ hydroxyalkyl or a di-(C$_{1-4}$)-[hydroxyalkyl]-(C$_{1-4}$)-aminoalkyl radical, an amino radical, a C$_{1-4}$ alkyl or a di-(C$_{1-4}$ hydroxyalkyl)-amino radical, a halogen atom, a carboxylic acid group or a sulfonic acid group, i has the value 0, 1, 2 or 3,
p has the value 0 or 1,
q has the value 0 or 1 and
n has the value 0 or 1, with the proviso that
the sum of p+q is not 0,
where p+q=2, n has the value 0 and the groups NG$^{17}$G$^{18}$ and NG$^{19}$G$^{20}$ occupy the (2,3); (5,6); (6,7); (3,5) or (3,7) positions;
where p+q=1, n has the value 1 and the groups NG$^{17}$G$^{18}$ (or NG$^{19}$G$^{20}$) and the group OH occupy the (2,3); (5,6); (6,7); (3,5) or (3,7) positions.

According to the invention, the substituents used in formula (E4) are as defined in the foregoing.

If the pyrazole-[1,5-a]-pyrimidine corresponding to formula (E4) above contains a hydroxy group in one of the positions 2, 5 or 7 of the ring system, a tautomeric equilibrium exists as illustrated, for example, in the following scheme:

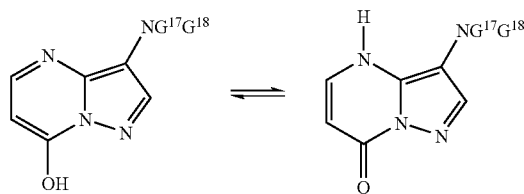

Among the pyrazole-[1,5-a]-pyrimidines corresponding to formula (E4) above, the following may be particularly mentioned:
pyrazole-[1,5-a]-pyrimidine-3,7-diamine;
2,5-dimethylpyrazole-[1,5-a]-pyrimidine-3,7-diamine;
pyrazole-[1,5-a]-pyrimidine-3,5-diamine;
2,7-dimethylpyrazole-[1,5-a]-pyrimidine-3,5-diamine;
3-aminopyrazole-[1,5-a]-pyrimidin-7-ol;
3-aminopyrazole-[1,5-a]-pyrimidin-5-ol;
2-(3-aminopyrazole-[1,5-a]-pyrimidin-7-ylamino)-ethanol;
2-(7-aminopyrazole-[1,5-a]-pyrimidin-3-ylamino)-ethanol;
2-[(3-aminopyrazole-[1,5-a]-pyrimidin-7-yl)-(2-hydroxyethyl)-amino]-ethanol;
2-[(7-aminopyrazole-[1,5-a]-pyrimidin-3-yl)-(2-hydroxyethyl)-amino]-ethanol;
5,6-dimethylpyrazole-[1,5-a]-pyrimidine-3,7-diamine;
2,6-dimethylpyrazole-[1,5-a]-pyrimidine-3,7-diamine;
2,5,N7,N7-tetramethylpyrazole-[1,5-a]-pyrimidine-3,7-diamine;

and physiologically compatible salts thereof and tautomeric forms thereof where a tautomeric equilibrium exists.

The pyrazole-[1,5-a]-pyrimidines corresponding to formula (E4) above may be prepared by cyclization from an aminopyrazole or from hydrazine, as described in the literature.

In addition, the preparations according to the invention may contain cationic dye precursors of the primary intermediate and/or secondary intermediate type as described, for example, in WO-A1-99/03 819, WO-A2-99/03 834, WO-A1-99/03 836, WO-A1-99/48 856, WO-A1-99/48 874, WO-A1-99/48 875, WO-A2-00/42 971, WO-A1-00/42 979, WO-A1-00/42 980, WO-A1-00/43 356, WO-A1-00/43 367, WO-A1-00/43 368, WO-A1-00/43 386, WO-A1-00/43 388, WO-A1-00/43 389, WO-A1-00/43 396, EP-A1-0 984 006, EP-A1-0 984 007 and EP-A1-0 989 128.

Particularly preferred cationic dye precursors are
[2-(2',5'-diaminophenoxy)-ethyl]-diethylmethyl ammonium chloride,
[2-(4'-aminophenylamino)-propyl]-trimethyl ammonium chloride,
[4-(4'-aminophenylamino)-pentyl]-diethyl-(2-hydroxyethyl)-ammonium chloride,
1-{[5'-amino-2'-(2''-hydroxyethylamino)-phenylcarbamoyl]-methyl}-1,4-dimethyl piperazin-1-ium chloride,
1,4-bis-I-{3-[3'-(2'',5''-diaminophenoxy)-propyl]-3H-imidazol-1-ium}-butane dichloride,
1,3-bis-[3'-(2'',5''-diaminophenoxy)-propyl]-3H-imidazol-1-ium chloride,
N,N'-bis-[3-N-methyl-4-N-(4'-aminoaniline)-ethyl]-1,1,4,4-tetramethyl diammonium
1,3-propane dibromide,
1,3-bis-1-{3-{3'-[(4''-amino-3''-methylaniline)-N-propyl]}-3H-imidazol-1-ium}-propane dichloride,
1,3-bis-1-{3-{3'-[(4''-aminoaniline)-N-propyl]}-3H-imidazol-1-ium}-propane dichloride,
1,3-bis-1-{3-{3'-[(4''-amino-2''-methylaniline)-N-propyl]}-3H-imidazol-1-ium}-propane dichloride,
3-[3-(4'-aminophenylamino)-propyl]-I-methyl-3H-imidazol-1-ium chloride,
[3-(2',5'-diaminophenoxy)-propyl]-3-methyl-3H-imidazol-1-ium chloride,
3-[3-(4'-amino-3'-methylphenylamino)-propyl]-I-methyl-3H-imidazol-1-ium chloride,
3-[3-(4'-amino-2'-methylphenylamino)-propyl]-I-methyl-3H-imidazol-1-ium chloride,
1-[2-(4'-amino-2'-methoxyphenylamino)-ethyl]-3-methyl-3H-imidazol-1-ium chloride,
3-[3-(4'-amino-2'-fluorophenylamino)-propyl]-I-methyl-3H-imidazol-1-ium chloride,
3-[3-(4'-amino-2'-cyanophenylamino)-propyl]-I-methyl-3H-imidazol-1-ium chloride,
3-[2-(2',5'-diaminophenyl)-ethyl]-I-methyl-3H-imidazol-1-ium chloride,
1-{2-[(4'-aminophenyl)-ethylamino]-ethyl}-3-methyl-3H-imidazol-1-ium chloride,
N,N-bis-[2-(3'-methyl-3H-imidazol-1-ium)-ethyl]-4-aminoaniline chloride,
3-[2-(4'-aminophenylamino)-butyl]-I-methyl-3H-imidazol-1-ium chloride,
[2-(2',4'-diaminophenoxy)-ethyl]-diethylmethyl ammonium chloride, 1-[3-(2',4'-diaminophenoxy)-propyl]-3-methyl-3H-imidazol-1-ium chloride,
1-[(3'-hydroxy-4'-methylphenylcarbamoyl)-methyl]-3-methyl-3H-imidazol-1-ium chloride,
1,4-bis-1-{3-[3-(2',4'-diaminophenoxy)-propyl]-3H-imidazol-1-ium}-butane dichloride,
3-[(3'-hydroxy-4'-methansulfonylaminophenylcarbamoyl)-methyl]-1-methyl-3H-imidazol-1-ium chloride,
3-[(3',5'-dichloro-2'-hydroxy-4'-methylphenylcarbamoyl)-methyl]-1-methyl-3H-imidazol-1-ium chloride,
1-[(3',5'-dichloro-2'-hydroxy-4'-methylphenylcarbamoyl)-methyl]-1,4-dimethyl piperazin-1-ium chloride,
3-[(4'-acetylamino-2'-hydroxyphenylcarbamoyl)-methyl]-1-methyl-3H-imidazol-1-ium chloride,
4-{3-[(3'-hydroxynaphthalene-2'-carbonyl)-amino]-propyl}-4-methyl-morpholin-4-ium iodide,
3-[(1'-hydroxynaphthalen-2'-ylcarbamoyl)-methyl]-1-methyl-3H-imidazol-1-ium chloride,
3-[(5'-acetylamino-1'-hydroxynaphthalen-2'-ylcarbamoyl)-methyl]-1-methyl-3H-imidazol-1-ium chloride,
3-[(1'-hydroxy-5'-methanesulfonylaminonaphthalen-2'-ylcarbamoyl)-methyl]-1-methyl-3H-imidazol-1-ium chloride,
[3-(4'-amino-2',5'-dimethyl-2H-pyrazol-3'-ylamino)-propyl]-(2-hydroxyethyl)-dimethylammonium chloride,
1,3-bis-[(2'-hydroxy-4'-methylphenylcarbamoyl)-methyl]-3H-imidazol-1-ium chloride,
1-[2-(6'-aminobenzo[1,3]dioxol-5'-ylamino)-ethyl]-3-methyl-3H-imidazol-1-ium chloride,
3-[2-(6'-aminobenzo[1,3]dioxol-5'-ylamino)-ethyl]-1-(4-{3-[2-(6"-amino-benzo[1,3]dioxol-5"-ylamino)-ethyl]-3H-imidazol-1-ium}-butyl)-3H-imidazol-1-ium dichloride,
3-[3-(3'-amino-5'-methylpyrazolo[1,5-a]pyrimidin-7'-ylamino)-propyl]-1-(2-hydroxyethyl)-3H-imidazol-1-ium chloride,
1,3-bis-1-{3-{3-[(2'-aminoaaniline)-N-propyl]}-3H-imidazol-1-ium}-propane dibromide,
N,N'-bis-[3-N-(2'-aminoaniline)-N-propyl]-1,1,3,3-tetramethyldiammonium 1,3-propane dibromide,
    3-[3-(2'-aminophenylamino)-propyl]-1-methyl-3H-imidazol-1-ium chloride,
    [2-(2'-aminophenylamino)-ethyl]-trimethylammonium chloride and
    3-(4'-hydroxy-1'-methyl-1H-indol-5'-ylmethyl)-1-methyl-pyridinium methosulfate.

According to the invention, other preferred colorants contain at least one secondary intermediate as a dye precursor. m-Phenylenediamine derivatives, naphthols, resorcinol and resorcinol derivatives, pyrazolones and m-aminophenol derivatives are generally used as secondary intermediates. Particularly suitable secondary intermediates are 1-naphthol, 1,5-, 2,7- and 1,7-dihydroxynaphthalene, 5-amino-2-methylphenol, m-aminophenol, resorcinol, resorcinol monomethyl ether, m-phenylenediamine, 1-phenyl-3-methyl-5-pyrazolone, 2,4-dichloro-3-aminophenol, 1,3-bis-(2,4-diaminophenoxy)-propane, 2-chlororesorcinol, 4-chlororesorcinol, 2-chloro-6-methyl-3-aminophenol, 2-amino-3-hydroxypyridine, 2-methyl resorcinol, 5-methyl resorcinol and 2-methyl-4-chloro-5-aminophenol.

According to the invention, preferred secondary intermediates are
    m-aminophenol and derivatives thereof such as, for example, 5-amino-2-methylphenol, 3-amino-2-chloro-6-methylphenol, 2-hydroxy-4-aminophenoxyethanol, 2,6-dimethyl-3-aminophenol, 3-trifluoroacetylamino-2-chloro-6-methylphenol, 5-amino-4-chloro-2-methylphenol, 5-amino-4-methoxy-2-methylphenol, 5-(2'-hydroxyethyl)-amino-2-methylphenol, 3-(diethylamino)-phenol, N-cyclopentyl-3-aminophenol, 1,3-dihydroxy-5-(methylamino)-benzene, 3-(ethylamino)-4-methylphenol and 2,4-dichloro-3-aminophenol,
    o-aminophenol and derivatives thereof,
    m-diaminobenzene and derivatives thereof such as, for example, 2,4-diaminophenoxyethanol, 1,3-bis-(2,4-diaminophenoxy)-propane, 1-methoxy-2-amino-4-(2'-hydroxyethylamino)-benzene, 1,3-bis-(2,4-diaminophenyl)-propane, 2,6-bis-(2-hydroxyethylamino)-1-methyl-benzene and 1-amino-3-bis-(2'-hydroxyethyl)-aminobenzene,
    o-diaminobenzene and derivatives thereof such as, for example, 3,4-diaminobenzoic acid and 2,3-diamino-1-methylbenzene,
    di- and trihydroxybenzene derivatives such as, for example, resorcinol, resorcinol monomethyl ether, 2-methyl resorcinol, 5-methyl resorcinol, 2,5-dimethyl resorcinol, 2-chlororesorcinol, 4-chlororesorcinol, pyrogallol and 1,2,4-trihydroxybenzene,
    pyridine derivatives such as, for example, 2,6-dihydroxypyridine, 2-amino-3-hydroxypyridine, 2-amino-5-chloro-3-hydroxypyridine, 3-amino-2-methylamino-6-methoxypyridine, 2,6-dihydroxy-3,4-dimethylpyridine, 2,6-dihydroxy-4-methylpyridine, 2,6-diaminopyridine, 2,3-diamino-6-methoxypyridine and 3,5-diamino-2,6-dimethoxypyridine,
    naphthalene derivatives such as, for example, 1-naphthol, 2-methyl-1-naphthol, 2-hydroxymethyl-1-naphthol, 2-hydroxyethyl-1-naphthol, 1,5-dihydroxynaphthalene, 1,6-dihydroxynaphthalene, 1,7-dihdroxy-naphthalene, 1,8-dihydroxynaphthalene, 2,7-dihdroxynaphthalene and 2,3-dihdroxynaphthalene,
    morpholine derivatives such as, for example, 6-hydroxybenzomorpholine and 6-aminobenzomorpholine,
    quinoxaline derivatives such as, for example, 6-methyl-1,2,3,4-tetrahydroquinoxaline,
    pyrazole derivatives such as, for example, 1-phenyl-3-methylpyrazol-5-one,
    indole derivatives such as, for example, 4-hydroxyindole, 6-hydroxyindole and 7-hydroxyindole,
    pyrimidine derivatives such as, for example, 4,6-diaminopyrimidine, 4-amino-2,6-dihydroxypyrimidine, 2,4-diamino-6-hydroxypyrimidine, 2,4,6-trihydroxypyrimidine, 2-amino-4-methylpyrimidine, 2-amino-4-hydroxy-6-methylpyrimidine and 4,6-dihydroxy-2-methylpyrimidine or
    methylenedioxybenzene derivatives such as, for example, 1-hydroxy-3,4-methylenedioxybenzene, 1-amino-3,4-methylenedioxybenzene and 1-(2'-hydroxyethyl)-amino-3,4-methylenedioxybenzene.

Particularly preferred secondary intermediates are 1-naphthol, 1,5-, 2,7- and 1,7-dihydroxynaphthalene, 3-aminophenol, 5-amino-2-methylphenol, 2-amino-3-hydroxypyridine, resorcinol, 4-chlororesorcinol, 2-chloro-6-methyl-3-aminophenol, 2-methyl resorcinol, 5-methyl resorcinol, 2,5-dimethyl resorcinol and 2,6-dihydroxy-3,4-dimethylpyridine.

If the dye precursors are amino compounds, the known acid addition salts may be prepared from them in the usual way. Accordingly, all statements in this specification and hence the claimed scope of protection relate both to the compounds present in free from and to their water-soluble physiologically compatible salts. Examples of such salts are the hydrochlorides, the hydrobromides, the sulfates, the phosphates, the acetates, the propionates, the citrates and the lactates.

The oxidation dye precursors of the primary/secondary intermediate type are present in the preparations according to the invention in quantities of preferably 0.01 to 20% by weight and more particularly 0.1 to 5% by weight, based on the preparation as a whole.

According to the invention, other preferred dye precursors are precursors of "nature-analogous" dyes. Preferred precursors of "nature-analogous" dyes are indoles and indolines which contain at least one hydroxy or amino group, preferably as a substituent on the six ring. These groups may carry further substituents, for example in the form of an etherification or esterification of the hydroxy group or an alkylation of the amino group. In a second preferred embodiment, the colorants contain at least one indole and/or indoline derivative.

Particularly suitable precursors of "nature-analogous" hair dyes are derivatives of 5,6-dihydroxyindoline corresponding to formula (Ia):

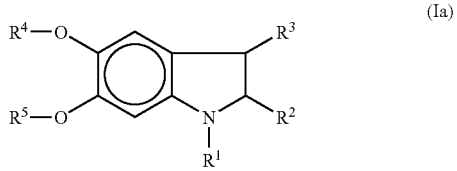

(Ia)

in which—independently of one another—
R$^1$ is hydrogen, a C$_{1-4}$ alkyl group, a C$_{1-4}$ hydroxyalkyl group or a C$_{2-4}$ polyhydroxyalkyl group,
R$^2$ is hydrogen or a —COOH group, the —COOH group optionally being present as a salt with a physiologically compatible cation,
R$^3$ is hydrogen or a C$_{1-4}$ alkyl group,
R$^4$ is hydrogen, a C$_{1-4}$ alkyl group or a group —CO—R$^6$, where R$^6$ is a C$_{1-4}$ alkyl group, and
R$^5$ is one of the groups mentioned for R$^4$, and physiologically compatible salts of these compounds with an organic or inorganic acid.

Particularly preferred derivatives of indoline are 5,6-dihydroxyindoline, N-methyl-5,6-dihydroxyindoline, N-ethyl-5,6-dihydroxyindoline, N-propyl-5,6-dihydroxyindoline, N-butyl-5,6-dihydroxyindoline, 5,6-dihydroxyindoline-2-carboxylic acid and 6-hydroxyindoline, 6-aminoindoline and 4-aminoindoline.

Within this group, particular emphasis is placed on N-methyl-5,6-dihydroxyindoline, N-ethyl-5,6-dihydroxyindoline, N-propyl-5,6-dihydroxyindoline, N-butyl-5,6-dihydroxyindoline and, in particular, 5,6-dihydroxyindoline.

Other particularly suitable precursors of "nature-analogous" hair dyes are derivatives of 5,6-dihydroxyindole corresponding to formula (Ib):

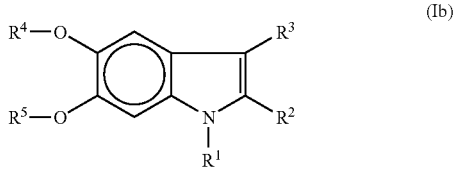

(Ib)

in which—independently of one another—
R$^1$ is hydrogen, a C$_{1-4}$ alkyl group or a C$_{1-4}$ hydroxyalkyl group,
R$^2$ is hydrogen or a —COOH group, the —COOH group optionally being present as a salt with a physiologically compatible cation,
R$^3$ is hydrogen or a C$_{1-4}$ alkyl group,
R$^4$ is hydrogen, a C$_{1-4}$ alkyl group or a group —CO—R$^6$, where R$^6$ is a C$_{1-4}$ alkyl group, and
R$^5$ is one of the groups mentioned for R$^4$, and physiologically compatible salts of these compounds with an organic or inorganic acid.

Particularly preferred derivatives of indole are 5,6-dihydroxyindole, N-methyl-5,6-dihydroxyindole, N-ethyl-5,6-dihydroxyindole, N-propyl-5,6-dihydroxyindole, N-butyl-5,6-dihydroxyindole, 5,6-dihydroxyindole-2-carboxylic acid, 6-hydroxyindole, 6-aminoindole and 4-aminoindole.

Within this group, particular emphasis is placed on N-methyl-5,6-dihydroxyindole, N-ethyl-5,6-dihydroxyindole, N-propyl-5,6-dihydroxyindole, N-butyl-5,6-dihydroxyindole and, in particular, 5,6-dihydroxyindole.

The indoline and indole derivatives may be used both as free bases and in the form of their physiologically compatible salts with inorganic or organic acids, for example hydrochlorides, sulfates and hydrobromides, in the colorants used in the process according to the invention. The indole or indoline derivatives are present in these colorants in quantities of normally 0.05 to 10% by weight and preferably 0.2 to 5% by weight.

In another preferred embodiment of the invention, the indoline or indole derivative may be used in combination with at least one amino acid or an oligopeptide in hair colorants. The amino acid is advantageously an α-amino acid. Most particularly preferred α-amino acids are arginine, ornithine, lysine, serine and histidine, especially arginine.

In a second preferred embodiment of the present invention, the colorants contain at least one substantive dye. It is irrelevant to the teaching according to the invention whether the colorant is based solely on substantive dyes or whether it contains substantive dyes in combination with the dye precursors mentioned above for the purpose of obtaining the required color effects.

Substantive dyes are typically nitrophenylenediamines, nitroaminophenols, azo dyes, anthraquinones or indophenols. Preferred substantive dyes are the compounds known under the International names or commercial names of HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 12, Disperse Blue 3, HC Violet 1, Disperse Violet 1, Disperse Violet 4, Acid Violet 43, Disperse Black 9 and Acid Black 52 and also 1,4-diamino-2-nitrobenzene, 2-amino-4-nitrophenol, 1,4-bis-(β-hydroxyethyl)-amino-2-nitrobenzene, 3-nitro-4-(β-hydroxyethyl)-aminophenol, 2-(2'-hydroxyethyl)-amino-4,6-dinitrophenol, 1-(2'-hydroxyethyl)-amino-4-methyl-2-nitrobenzene, 1-amino-4-(2'-hydroxyethyl)-amino-5-chloro-2-nitrobenzene, 4-amino-3-nitrophenol, 1-(2'-ureidoethyl)-amino-4-nitrobenzene, 4-amino-2-nitrodiphenylamine-2'-carboxylic acid, 6-nitro-1,2,3,4-tetrahydroquinoxaline, 2-hydroxy-1,4-naphthoquinone, hydroxyethyl-2-nitrotoluidine, picramic acid and salts thereof, 2-amino-6-chloro-4-nitrophenol, 4-ethylamino-3-nitrobenzoic acid and 2-chloro-6-ethylamino-1-hydroxy-4-nitrobenzene.

In addition, the preparations according to the invention may contain a cationic substantive dye. Particularly preferred are (i) cationic triphenylmethane dyes such as, for example, Basic Blue 7, Basic Blue 26, Basic Violet 2 and Basic Violet 14,
(ii) aromatic systems substituted by a quaternary nitrogen group such as, for example, Basic Yellow 57, Basic Red 76, Basic Blue 99, Basic Brown 16 and Basic Brown 17 and
(iii) substantive dyes containing a heterocycle with at least one quaternary nitrogen atom as disclosed, for example, in EP-A2 998 908, to which reference is specifically made at this juncture, in claims 6 to 11.

Preferred cationic substantive dyes of group (iii) are, in particular, the following compounds:

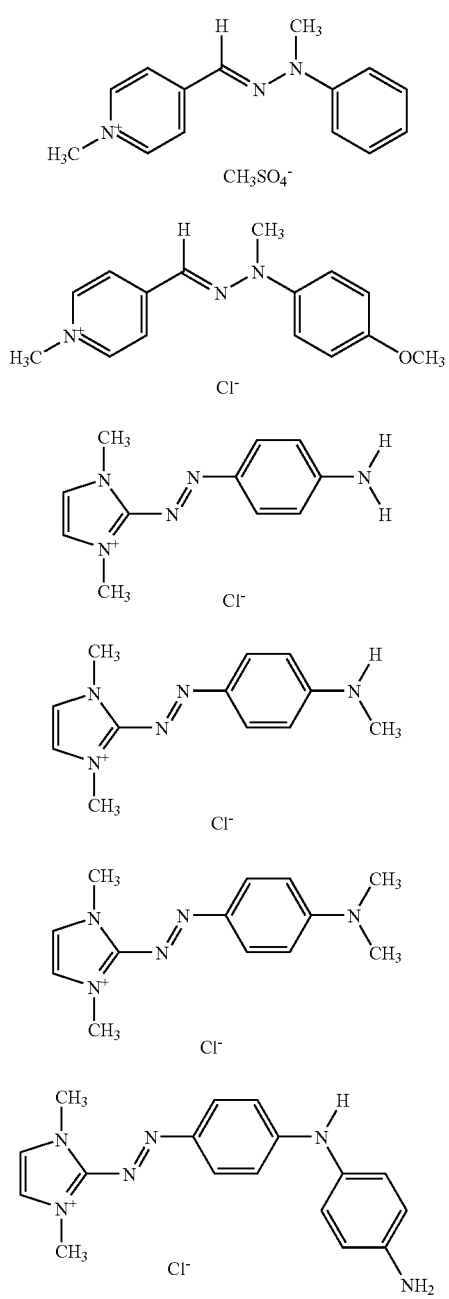

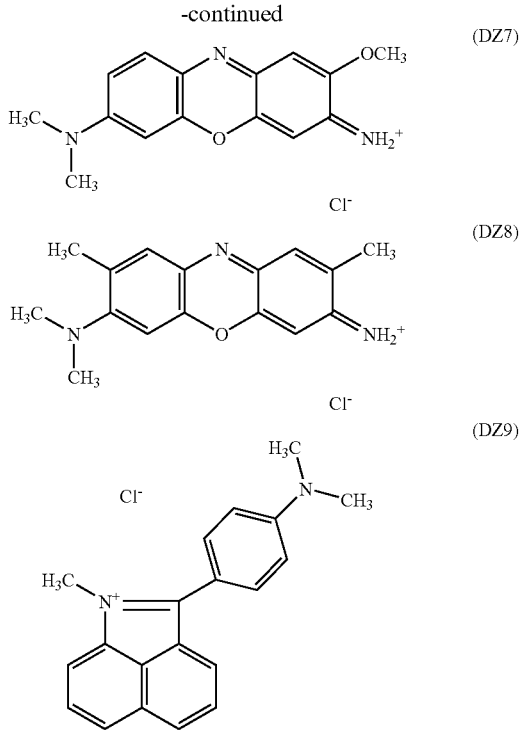

The compounds corresponding to formula (DZ1), (DZ3) and (DZ5) are most particularly preferred cationic substantive dyes of group (iii).

The preparations according to the invention of this embodiment contain the substantive dyes in a quantity of preferably 0.01 to 20% by weight, based on the colorant as a whole.

The preparations according to the invention may also contain naturally occurring dyes such as, for example, henna red, henna neutral, henna black, camomile blossom, sandalwood, black tea, black alder bark, sage, logwood, madder root, catechu, sedre and alkanet.

The oxidation dye precursors or the substantive dyes do not have to be single compounds. On the contrary, other components may be present in small quantities in the hair colorants according to the invention due to the processes used to produce the individual dyes providing these other components do not adversely affect the coloring result or have to be ruled out for other reasons, for example toxicological reasons.

So far as the dyes suitable for use in the hair colorants and tinting preparations according to the invention are concerned, reference is also expressly made to the work by Ch. Zviak, The Science of Hair Care, Chapter 7 (pages 248–250; substantive dyes) and Chapter 8, pages 264–267; oxidation dye precursors), published as Volume 7 of the Series "Dermatology" (Ed.: Ch. Culnan and H. Maibach), Marcel Dekker Inc., New York/Basle, 1986, and to the "Europäische Inventar der Kosmetik-Rohstoffe" published by the Europäische Gemeinschaft and available in disk form from the Bundesverband Deutscher Industrie—und Handelsunternehmen für Arzneimittel, Reformwaren und Körperpflegemittel d.V., Mannheim.

Hair colorants are normally adjusted to a mildly acidic to alkaline pH, i.e. to a pH of about 5 to 11, particularly where coloring is carried out oxidatively with atmospheric oxygen or other oxidizing agents, such as hydrogen peroxide. To this end, the colorants contain alkalizing agents, normally alkali metal or alkaline earth metal hydroxides, ammonia or organic amines. Preferred alkalizing agents are monoethanolamine, monoisopropanolamine, 2-amino-2-methylpropanol, 2-amino-2-methylpropane-1,3-diol, 2-amino-2-ethylpropane-1,3-diol, 2-amino-2-methylbutanol and triethanolamine and alkali metal and alkaline earth metal hydroxides. Within this group, monoethanolamine, triethanolamine and 2-amino-2-methylpropanol and 2-amino-2-methylpropane-1,3-diol are preferred. ω-Amino acids, such as ω-aminocaproic acid, may also be used as alkalizing agents. Ammonia is a most partly preferred alkalizing agent.

If the actual hair colors are formed in an oxidative process, typical oxidizing agents such as, in particular, hydrogen peroxide or adducts thereof with urea, melamine or sodium borate may be used. However, oxidation with atmospheric oxygen as sole oxidizing agent may be preferred. Oxidation may also be carried out with enzymes. In this case, the enzymes may be used both to produce oxidizing per compounds and to enhance the effect of an oxidizing agent present in small quantities. Thus, the enzymes (enzyme class 1: oxidoreductases) are capable of transferring electrons from suitable primary intermediates (reducing agents) to atmospheric oxygen. Preferred enzymes are oxidases, such as tyrosinase and laccase, although glucoseoxidase, uricase or pyruvate oxidase may also be used. Mention is also made of the procedure whereby the effect of small quantities (for example 1% and less, based on the composition as a whole) of hydrogen peroxide is strengthened by peroxidases.

In the particular case of hair which is difficult to color, the preparation containing the oxidation dye precursors may be applied to the hair without preliminary mixing with the oxidation component. The oxidation component is applied after a contact time of 20 to 30 minutes, optionally after rinsing. After another contact time of 10 to 20 minutes, the hair is rinsed and, if desired, shampooed. In a first variant of this embodiment where the preliminary application of the dye precursors is intended to improve penetration into the hair, the corresponding formulation is adjusted to a pH value of about 4 to 7. In a second variant, oxidation with air is initially carried out, the formulation applied preferably having a pH value of 7 to 10. In the subsequent accelerated post-oxidation phase, it can be of advantage to use acidified peroxydisulfate solutions as the oxidizing agent.

Whichever of the procedures is used in the process according to the invention, development of the color may be supported and enhanced by adding certain metal ions to the colorant. Examples of such metal ions are $Zn^{2+}$, $Cu^{2+}$, $Fe^{2+}$, $Fe^{3+}$, $Mn^{2+}$, $Mn^{4+}$, $Li^+$, $Mg^{2+}$, $Ca^{2+}$ and $Al^{3+}$. $Zn^{2+}$, $Cu^{2+}$ and $Mn^{2+}$ are particularly suitable. Basically, the metal ions may be used in the form of a physiologically compatible salt. Preferred salts are the acetates, sulfates, halides, lactates and tartrates. Development of the hair color can be accelerated and the color tone can be influenced as required through the use of these metal salts.

Irrespective of the nature of the colorant, it is preferred in accordance with the invention to mix the colorant with an oxidizing agent preparation immediately before application.

In a second embodiment, therefore, the present invention relates to a process for coloring keratin fibers in which one of the preparations according to the invention is mixed with an oxidizing agent preparation immediately before application, the resulting preparation is applied to the fibers and is then rinsed off again after a contact time.

In another embodiment of the present invention, pure coloring cream is first applied to the hair and, after a contact time, a preparation obtainable by mixing the actual coloring cream with an oxidizing agent preparation is applied.

In a third embodiment, therefore, the present invention relates to a process for coloring keratin fibers in which one of the preparations according to the invention is applied to the fibers; after a contact time, a second preparation obtained by mixing one of the preparations according to the invention with an oxidizing agent preparation immediately before application is applied to the fibers and, after a further contact time, the fibers are thoroughly rinsed.

Although, in principle, any of the oxidizing agents known in the coloring of hair may be used, hydrogen peroxide is preferably used in accordance with the invention. The oxidizing agent preparation based on hydrogen peroxide preferably has a pH of 1 to 6 and more particularly 2 to 4. The dye (precursor) preparation and the oxidizing agent preparation are normally mixed in a quantity ratio of 4:1 to 1:3 and more particularly 2:1 to 1:1 immediately before application. The resulting preparation for application to the hair should preferably have a pH of 6 to 12 and more particularly 9 to 11. In a particularly preferred embodiment, the hair colorant is applied in a weakly alkaline medium. The application temperatures may be in the range from 10 to 60° C. and, in one particular embodiment, are in the range from 15 to 40° C. The preparation is preferably applied at the temperature of the scalp. To shorten the contact time or to improve the coloring result, the preparation may be applied in the presence of heat, for example under a drying hood. After a contact time of ca. 5 to 60 and more particularly 15 to 30 minutes, the hair colorant is removed from the hair to be colored by rinsing. There is no need for washing with a shampoo where a carrier of high surfactant content, for example a coloring shampoo, has been used.

In a preferred embodiment of the invention, the preparation applied to the hair contains at least one other quaternary ammonium compound. According to the invention, this quaternary ammonium compound may be a constituent of the coloring cream and/or the oxidizing agent preparation. In a preferred embodiment, however, the other quaternary ammonium compound is a constituent of the oxidizing agent preparation.

Preferred quaternary ammonium compounds are ammonium halides, more particularly chlorides and bromides, such as alkyl trimethyl ammonium chlorides, dialkyl dimethyl ammonium chlorides and trialkyl methyl ammonium chlorides, for example cetyl trimethyl ammonium chloride, stearyl trimethyl ammonium chloride, behenyl trimethyl ammonium chloride, distearyl dimethyl ammonium chloride, lauryl dimethyl ammonium chloride, lauryl dimethyl benzyl ammonium chloride and tricetyl methyl ammonium chloride and the imidazolium compounds known under the INCI names of Quaternium-27 and Quaternium-83. The long alkyl chains of the above-mentioned surfactants preferably contain 10 to 18 carbon atoms. Stearyl trimethyl ammonium chloride is particularly preferred.

However, other preferred quaternary ammonium compounds are the so-called esterquats. Esterquats are known substances which contain both at least one ester function and at least one quaternary ammonium group as structural element. Preferred esterquats are quaternized ester salts of fatty acids with triethanolamine, quaternized ester salts of fatty acids with diethanol alkylamines and quaternized ester salts of fatty acids with 1,2-dihydroxypropyl dialkylamines. Such products are marketed, for example, under the names of Stepantex®, Dehyquart® and Armocare®. The products Armocare® VGH-70, an N,N-bis-(2-palmitoyloxyethyl)-dimethyl ammonium chloride, and Dehyquart® F-75, Dehyquart® C-4046, Dehyquart® L80 and Dehyquart® AU-35 are examples of such esterquats.

According to the invention, other preferred quaternary ammonium compounds are the alkyl amidoamines. The alkyl amidoamines are normally prepared by amidation of natural or synthetic fatty acids and fatty acid cuts with dialkyl aminoamines. A compound from this group particularly suitable for the purposes of the invention is the stearamidopropyl dimethylamine obtainable under the name of Tegoamid® S 18.

In a fourth embodiment, the present invention relates to a two-component kit for coloring keratin fibers comprising a first preparation according to any of claims 1 to 18 and a second preparation containing at least one oxidizing agent and at least one other quaternary ammonium compound.

So far as the oxidizing agents and other quaternary ammonium compounds suitable for use in this fourth embodiment are concerned, reference is made to the foregoing observations.

The preparations according to the invention may also contain any of the known active substances, additives and auxiliaries typical of such formulations. In many cases, the preparations contain at least one surfactant, both anionic and zwitterionic, ampholytic, nonionic and cationic surfactants being suitable in principle. In many cases, however, it has proved to be of advantage to select the surfactants from anionic, zwitterionic or nonionic surfactants.

Suitable anionic surfactants for the preparations according to the invention are any anionic surface-active substances suitable for use on the human body. Such substances are characterized by a water-solubilizing anionic group such as, for example, a carboxylate, sulfate, sulfonate or phosphate group and a lipophilic alkyl group containing around 10 to 22 carbon atoms. In addition, glycol or polyglycol ether groups, ester, ether and amide and hydroxyl groups may also be present in the molecule. The following are examples of suitable anionic surfactants—in the form of the sodium, potassium and ammonium salts and the mono-, di- and trialkanol-ammonium salts containing 2 or 3 carbon atoms in the alkanol group:

linear fatty acids containing 10 to 22 carbon atoms (soaps),
ether carboxylic acids corresponding to the formula R—O—(CH$_2$—CH$_2$O)$_x$—CH$_2$—COOH, in which R is a linear alkyl group containing 10 to 22 carbon atoms and x=0 or 1 to 16,
acyl sarcosides containing 10 to 18 carbon atoms in the acyl group,
acyl taurides containing 10 to 18 carbon atoms in the acyl group,
acyl isethionates containing 10 to 18 carbon atoms in the acyl group,
sulfosuccinic acid mono- and dialkyl esters containing 8 to 18 carbon atoms in the alkyl group and sulfosuccinic acid monoalkyl polyoxyethyl esters containing 8 to 18 carbon atoms in the alkyl group and 1 to 6 oxyethyl groups,
linear alkane sulfonates containing 12 to 18 carbon atoms,
linear α-olefin sulfonates containing 12 to 18 carbon atoms,
α-sulfofatty acid methyl esters of fatty acids containing 12 to 18 carbon atoms,
alkyl sulfates and alkyl polyglycol ether sulfates corresponding to the formula R—O(CH$_2$—CH$_2$O)$_x$—SO$_3$H, in which R is a preferably linear alkyl group containing 10 to 18 carbon atoms and x=0 or 1 to 12,
mixtures of surface-active hydroxysulfonates according to DE-A-37 25 030,
sulfated hydroxyalkyl polyethylene and/or hydroxyalkylene propylene glycol ethers according to DE-A-37 23 354,
sulfonates of unsaturated fatty acids containing 12 to 24 carbon atoms and 1 to 6 double bonds according to DE-A-39 26 344,
esters of tartaric acid and citric acid with alcohols in the form of addition products of around 2 to 15 mol ethylene oxide and/or propylene oxide with fatty alcohols containing 8 to 22 carbon atoms.

Preferred anionic surfactants are alkyl sulfates, alkyl polyglycol ether sulfates and ether carboxylic acids containing 10 to 18 carbon atoms in the alkyl group and up to 12 glycol ether groups in the molecule and, in particular, salts of saturated and, more particularly, unsaturated C$_{8-22}$ carboxylic acids, such as oleic acid, stearic acid, isostearic acid and palmitic acid.

Nonionic surfactants contain, for example, a polyol group, a polyalkylene glycol ether group or a combination of polyol and polyglycol ether groups as the hydrophilic group. Examples of such compounds are products of the addition of 2 to 30 mol ethylene oxide and/or 0 to 5 mol propylene oxide onto linear fatty alcohols containing 8 to 22 carbon atoms, onto fatty acids containing 12 to 22 carbon atoms and onto alkylphenols containing 8 to 15 carbon atoms in the alkyl group,
C$_{12-22}$ fatty acid monoesters and diesters of products of the addition of 1 to 30 mol ethylene oxide onto glycerol,
C$_{8-22}$ alkyl mono- and oligoglycosides and ethoxylated analogs thereof and
products of the addition of 5 to 60 mol ethylene oxide onto castor oil and hydrogenated castor oil.

Preferred nonionic surfactants are alkyl polyglycosides corresponding to the general formula R$^1$O-(Z)$_x$. These compounds are characterized by the following parameters.

The alkyl group R$^1$ contains 6 to 22 carbon atoms and may be both linear and branched. Primary linear and 2-methyl-branched aliphatic groups are preferred. Such alkyl groups are, for example, 1-octyl, 1-decyl, 1-lauryl, 1-myristyl, 1-cetyl and 1-stearyl. 1-Octyl, 1-decyl, 1-lauryl and 1-myristyl are particularly preferred. Where so-called "oxo alcohols" are used as starting materials, compounds with an odd number of carbon atoms in the alkyl chain predominate.

The alkyl polyglyosides suitable for use in accordance with the invention may, for example, contain only one particular alkyl group R$^1$. However, such compounds are normally prepared from natural fats and oils or mineral oils. In this case, mixtures corresponding to the starting compounds or corresponding to the particular working up of these compounds are present as the alkyl groups R$^1$.

Particularly preferred alkyl polyglycosides are those in which R$^1$ consists
  essentially of C$_8$ and C$_{10}$ alkyl groups,
  essentially of C$_{12}$ and C$_{14}$ alkyl groups,
  essentially of C$_8$ to C$_{16}$ alkyl groups or
  essentially of C$_{12}$ to C$_{16}$ alkyl groups.

Any mono- or oligosaccharides may be used as the sugar unit Z. Sugars containing 5 or 6 carbon atoms and the corresponding oligosaccharides are normally used. Examples of such sugars are glucose, fructose, galactose, arabinose, ribose, xylose, lyxose, allose, altrose, mannose, gulose, idose, talose and sucrose. Preferred sugar units are glucose, fructose, galactose, arabinose and sucrose; glucose is particularly preferred.

The alkyl polyglycosides suitable for use in accordance with the invention contain on average 1.1 to 5 sugar units.

Alkyl polyglycosides with x values of 1.1 to 1.6 are preferred. Alkyl oligoglycosides where x is 1.1 to 1.4 are most particularly preferred.

Besides acting as surfactants, the alkyl polyglycosides or alkyl oligoglycosides may also be used to improve the fixing of perfume components to the hair. Accordingly, in cases where the effect of the perfume oil on the hair is intended to last longer than the duration of the hair treatment, alkyl poly- or oligoglycosides will preferably be used as another ingredient of the preparations according to the invention.

Alkoxylated homologs of the alkyl polyglycosides mentioned may also be used in accordance with the invention. These homologs may contain on average up to 10 ethylene oxide and/or propylene oxide units per alkyl glycoside unit.

Zwitterionic surfactants may also be used, particularly as co-surfactants. In the context of the invention, zwitterionic surfactants are surface-active compounds which contain at least one quaternary ammonium group and at least one —$COO^{(-)}$ or —$SO_3^{(-)}$ group in the molecule. Particularly suitable zwitterionic surfactants are the so-called betaines, such as N-alkyl-N,N-dimethyl ammonium glycinates, for example cocoalkyl dimethyl ammonium glycinate, N-acylaminopropyl-N,N-dimethyl ammonium glycinates, cocoacylaminopropyl dimethyl ammonium glycinate and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. A preferred zwitterionic surfactant is the fatty acid amide derivative known by the INCI name of Cocamidopropyl Betaine.

Also suitable, particularly as co-surfactants, are ampholytic surfactants. Ampholytic surfactants are surface-active compounds which, in addition to a $C_{8-18}$ alkyl or acyl group, contain at least one free amino group and at least one —COOH or —$SO_3H$ group in the molecule and which are capable of forming inner salts. Examples of suitable ampholytic surfactants are N-alkyl glycines, N-alkyl propionic acids, N-alkyl aminobutyric acids, N-alkyl iminodipropionic acids, N-hydroxyethyl-N-alkyl amidopropyl glycines, N-alkyl taurines, N-alkyl sarcosines, 2-alkyl aminopropionic acids and alkyl aminoacetic acids containing around 8 to 18 carbon atoms in the alkyl group. Particularly preferred ampholytic surfactants are N-cocoalkyl aminopropionate, cocoacyl aminoethyl aminopropionate and $C_{12-18}$ acyl sarcosine.

Besides the quaternary ammonium compounds mentioned above, quaternized protein hydrolyzates represent other cationic surfactants suitable for use in accordance with the invention.

One example of a quaternary sugar derivative suitable for use as a cationic surfactant is the commercially available product Glucquat®100 (INCI name: Lauryl Methyl Gluceth-10 Hydroxypropyl Dimonium Chloride).

The compounds containing alkyl groups used as surfactants may be single compounds. In general, however, these compounds are produced from native vegetable or animal raw materials so that mixtures with different alkyl chain lengths dependent upon the particular raw material are obtained.

The surfactants representing addition products of ethylene and/or propylene oxide with fatty alcohols or derivatives of these addition products may be both products with a "normal" homolog distribution and products with a narrow homolog distribution. Products with a "normal" homolog distribution are mixtures of homologs which are obtained in the reaction of fatty alcohol and alkylene oxide using alkali metals, alkali metal hydroxides or alkali metal alcoholates as catalysts. By contrast, narrow homolog distributions are obtained when, for example, hydrotalcites, alkaline earth metal salts of ether carboxylic acids, alkaline earth metal oxides, hydroxides or alcoholates are used as catalysts. The use of products with a narrow homolog distribution can be of advantage.

In addition, the colorants according to the invention may preferably contain another conditioning agent selected from the group consisting of cationic surfactants, cationic polymers, alkyl amidoamines, paraffin oils, vegetable oils and synthetic oils.

Preferred conditioning agents include cationic polymers. These are generally polymers which contain a quaternary nitrogen atom, for example in the form of an ammonium group.

Preferred cationic polymers are, for example, the quaternized cellulose derivatives commercially available under the names of Celquat® and Polymer JR®. The compounds Celquat® H 100, Celquat® L 200 and Polymer JR® 400 are preferred quaternized cellulose derivatives, copolymers of vinyl pyrrolidone with quaternized derivatives of dialkylaminoacrylate and methacrylate such as, for example, vinyl pyrrolidone/dimethylaminoethyl methacrylate copolymers quaternized with diethyl sulfate. Such compounds are commercially available under the names of Gafquat® 734 and Gafquat® 755, the vinyl pyrrolidone/vinyl imidazolinium methochloride copolymers commercially available under the name of Luviquat®, quaternized polyvinyl alcohol;

and the polymers containing quaternary nitrogen atoms in the main polymer chain known under the names of Polyquaternium 2, Polyquaternium 17, Polyquaternium 18 and Polyquaternium 27.

Cationic polymers belonging to the first four groups mentioned are particularly preferred; Polyquaternium 2, Polyquaternium 10 and Polyquaternium 22 are most particularly preferred.

Other suitable conditioning agents are paraffin oils, synthetically produced oligomeric alkenes and vegetable oils, such as jojoba oil, sunflower oil, orange oil, almond oil, wheatgerm oil and peach kernel oil.

Phospholipids, for example soya lecithin, egg lecithin and kephalins, are also suitable hair-conditioning compounds, as are the substances known under the INCI names of Linoleamidopropyl PG-Dimonium Chloride Phosphate, Cocamidopropyl PG-Dimonium Chloride Phophate and Stearamido PG-Dimonium Chloride Phosphate. These substances are marketed, for example, by Mona under the name of Phospholipid EFA®, Phospholipid PTC® and Phospholipid SV®.

Other active substances, auxiliaries and additives are, for example, nonionic polymers such as, for example, vinyl pyrrolidone/vinyl acrylate copolymers, polyvinyl pyrrolidone and vinyl pyrrolidone/vinyl acetate copolymers and polysiloxanes, zwifterionic and amphoteric polymers such as, for example, acrylamido-propyl/trimethyl ammonium chloride/acrylate copolymers and octyl acrylamide/methyl methacrylate/tert.butyl aminoethyl methacrylate/2-hydroxypropyl methacrylate copolymers, anionic polymers such as, for example, polyacrylic acids, crosslinked polyacrylic acids, vinyl acetate/crotonic acid copolymers, vinyl pyrrolidone/vinyl acrylate copolymers, vinyl acetate/butyl maleate/isobornyl acrylate copolymers, methyl vinyl ether/maleic anhydride copolymers and acrylic acid/ethyl acrylate/N-tert.butyl acrylamide terpolymers, thickeners, such as agar agar, guar gum, alginates, xanthan gum, gum arabic, karaya gum, locust bean gum, linseed gums, dextrans, cellulose derivatives, for example methyl cellulose, hydroxyalkyl cellulose and carboxymethyl cellulose, starch fractions and derivatives, such as amylose, amylopectin and dextrins, clays such as, for example, bentonite or fully synthetic hydrocolloids such as, for example, polyvinyl alcohol, structurants, such as maleic acid and lactic acid, protein hydrolyzates, more particularly elastin, collagen, keratin, milk protein, soya protein and wheat protein hydrolyzates, condensation products thereof with fatty acids and quaternized protein hydrolyzates, perfume oils, dimethyl isosorbide and cyclodextrins, solvents and solubilizers, such as ethanol, isopropanol, ethylene glycol, propylene glycol, glycerol and diethylene glycol, fiber-structure-improving agents, more particularly mono-, di- and oligosaccharides such as, for example, glucose, galactose, fructose and lactose, quaternized amines, such as methyl-1-alkylamidoethyl-2-alkylimidazolinium methosulfate, defoamers, such as silicones, dyes for coloring the preparation, antidandruff agents, such as piroctone olamine, zinc omadine and climbazol, UV filters, more particularly derivatized benzophenones, cinnamic acid derivatives and triazines, substances for adjusting the pH value, for example typical acids, more particularly food-grade acids and bases, active substances, such as allantoin, pyrrolidone carboxylic acids and salts thereof and bisabolol, vitamins, provitamins and vitamin precursors, more particularly those of groups A, $B_3$, $B_5$, $B_6$, C, E, F and H, plant extracts, such as the extracts of green tea, oak bark, stinging nettle, hamamelis, hops, camomile, burdock root, horse willow, hawthorn, lime blossom, almond, aloe vera, pine needle, horse chestnut, sandalwood, juniper, coconut, mango, apricot, lemon, wheat, kiwi, melon, orange, grapefruit, sage, rosemary, birch, mallow, lady's smock, creeping thyme, yarrow, thyme, balm, restharrow, coltsfoot, hibiscus, meristem, ginseng and ginger root, cholesterol, consistency factors, such as sugar esters, polyol esters or polyol alkyl ethers, fats and waxes, such as spermaceti, beeswax, montan wax and paraffins, fatty acid alkanolamides, complexing agents, such as EDTA, NTA, β-alanine diacetic acid and phosphonic acids, swelling and penetration agents, such as glycerol, propylene glycol monoethyl ether, carbonates, hydrogen carbonates, guanidines, ureas and primary, secondary and tertiary phosphates, opacifiers, such as latex, styrene/PVP and styrene/acrylamide copolymers, pearlizers, such as ethylene glycol mono- and distearate and PEG-3-distearate, pigments, stabilizers for hydrogen peroxide and other oxidizing agents, propellents, such as propane/butane mixtures, $N_2O$, dimethyl ether, $CO_2$ and air, antioxidants.

Information on other optional components and the quantities in which they are used can be found in the reference books known to the expert, for example Kh. Schrader, Grundlagen und Rezepturen der Kosmetika, 2nd Edition, Hüthig Buch Verlag, Heidelberg, 1989.

The following Examples are intended to illustrate the invention.

EXAMPLES

The quantities mentioned in the following are percentages by weight unless otherwise indicated.

The following coloring creams 1 to 8 were prepared.

Example 1

| Raw material | Quantity |
| --- | --- |
| Aqueous ammonium carbopol solution (1%) | 15.0 |
| Lanette ® E[1] | 0.70 |
| Sodium lauryl ether sulfate (27% aqueous solution) | 4.40 |
| PEG 400 | 0.60 |
| Potassium oleate (12.5% aqueous solution) | 3.00 |
| Titanium dioxide | 0.50 |
| Cetylstearyl alcohol 50/50 | 12.00 |
| Eumulgin ® B2[2] | 3.00 |
| Eutanol ® G[3] | 2.00 |
| Cutina ® AGS[4] | 2.00 |
| Cutina ® GMS-SE[5] | 2.00 |
| XF42-B1989[6] | 1.50 |
| Potassium hydroxide (50% in water) | 0.48 |
| Tetrasodium EDTA | 0.40 |
| Sodium sulfite | 0.10 |
| Ascorbic acid | 0.05 |
| Merquat Plus ® 3330[7] | 2.00 |
| Perfume | 0.50 |
| Ammonia (25% aqueous solution) | 6.00 |
| Aerosil ® 200[8] | 0.25 |
| p-Tolulyenediamine sulfate | 0.460 |
| Resorcinol | 0.200 |
| m-Aminophenol | 0.026 |
| 2,6-Diaminopyridine | 0.010 |
| 2,4-Diaminophenoxyethanol dihydrochloride | 0.012 |
| Water | to 100 |

[1]cetylstearyl alcohol sulfate sodium salt (NCI name: Sodium Cetearyl Sulfate) (Cognis)
[2]cetylstearyl alcohol containing ca. 20 EO units (INCI name: Ceteareth-20) (Cognis)
[3]2-octyl dodecyl alcohol (INCI name: Octyldodecanol) (Cognis)
[4]ethylene glycol distearate (INCI name: Glycol Distearate) (Cognis)
[5]glycerol mono-/distearate/potassium stearate mixture based on vegetable raw materials (INCI name: Glyceryl Stearate SE) (Cognis)
[6]aminofunctional silicone (INCI name: Amodimethicone) (GE Toshiba Silicones)
[7]dimethyldiallyl ammonium chloride/acrylic acid/acrylamide terpolymer (ca. 9.5% active substance content; INCI name: Polyquaternium-39) (Nalco)
[8]pyrogenic silica (INCI name: Silica) (Degussa)

Examples 2 to 4

| | Example | | |
| --- | --- | --- | --- |
| Raw material | 2 Quantity | 3 Quantity | 4 Quantity |
| Aqueous ammonium carbopol solution (1%) | 15.00 | 15.00 | 15.00 |
| Lanette ® E | 0.70 | 0.70 | 0.70 |

Examples 2 to 4 (continued)

| Raw material | Example 2 Quantity | Example 3 Quantity | Example 4 Quantity |
|---|---|---|---|
| Sodium laurylether sulfate (27% aqueous solution) | 4.40 | 4.40 | 4.40 |
| PEG 400 | 0.60 | 4.60 | 4.60 |
| Potassium oleate (12.5% aqueous solution) | 3.00 | 3.00 | 3.00 |
| Titanium dioxide | 0.50 | 0.50 | 0.50 |
| Cetylstearyl alcohol 50/50 | 12.00 | 12.00 | 12.00 |
| Eumulgin ® B2 | 3.00 | 3.00 | 3.00 |
| Eutanol ® G | 2.00 | 2.00 | 2.00 |
| Cutina ® AGS | 2.00 | 2.00 | 2.00 |
| Cutina ® GMS-ES | 2.00 | 2.00 | 2.00 |
| XF42-B1989 | 1.50 | 1.50 | 1.50 |
| Potassium hydroxide 50% | 1.00 | — | — |
| Tetrasodium EDTA | 0.40 | 0.40 | 0.40 |
| Sodium sulfite | 0.15 | — | — |
| Ascorbic acid | 0.10 | 0.05 | 0.05 |
| Merquat Plus ® 3330 | 2.00 | 2.00 | 2.00 |
| Perfume | 0.50 | 0.50 | 0.60 |
| AMP-100[9] | — | 3.94 | 7.80 |
| Ammonia (25% aqueous solution) | 6.00 | 6.00 | 7.50 |
| Aerosil ® 200 | 0.25 | 0.25 | 0.25 |
| p-Aminophenol | 0.200 | — | — |
| p-Toluylenediamine sulfate | 0.960 | — | — |
| Resorcinol | 0.450 | — | — |
| m-Aminophenol | 0.030 | — | — |
| 5-Amino-2-methylphenol | 0.060 | — | — |
| 1,2-Diamio-4-nitrobenzene | — | 0.350 | 0.400 |
| Water | to 100 | to 100 | to 100 |

[9] 2-amino-2-methylpropanol (INCI name: Aminomethyl Propanol) (CSC Chemie)

Example 5

| Raw material | Quantity |
|---|---|
| Aqueous ammonium carbopol solution (1%) | 15.00 |
| Lanette ® E | 0.70 |
| Sodium lauryl ether sulfate (27% aqueous solution) | 4.40 |
| PEG 400 | 0.60 |
| Potassium oleate (12.5% aqueous solution) | 3.00 |
| Titanium dioxide | 0.50 |
| Cetylstearyl alcohol 50/50 | 12.00 |
| Eumulgin ® B2 | 3.00 |
| Eutanol ® G | 2.00 |
| Cutina ® AGS | 2.00 |
| Cutina ® GMS-SE | 2.00 |
| XF42-B1989 | 1.50 |
| Potassium hydroxide (50% in water) | 0.28 |
| Tetrasodium EDTA | 0.40 |
| Sodium sulfite | 0.10 |
| Ascorbic acid | 0.05 |
| Merquat Plus ® 3330 | 2.00 |
| Perfume | 0.50 |
| AMP-100 | 5.00 |
| Ammonia (25% aqueous solution) | 6.50 |
| Aerosil ® 200 | 0.25 |
| p-Aminophenol | 0.015 |
| p-Toluylenediamine sulfate | 0.260 |
| 5-Amino-2-methylphenol | 0.250 |
| 2,4-Diaminophenoxyethanol dihydrochloride | 0.020 |
| Water | to 100 |

Examples 6 to 8

| Raw material | Example 6 Quantity | Example 7 Quantity | Example 8 Quantity |
|---|---|---|---|
| Aqueous ammonium carbopol solution (1%) | 15.00 | 15.00 | 15.00 |
| Lanette ® E | 0.70 | 0.70 | 0.70 |
| Sodium laurylether sulfate (27% aqueous solution) | 4.40 | 4.40 | 4.40 |
| PEG 400 | 0.60 | 0.60 | 0.60 |
| Potassium oleate (12.5% aqueous solution) | 3.00 | 3.00 | 3.00 |
| Titanium dioxide | 0.50 | 0.50 | 0.50 |
| Cetylstearyl alcohol 50/50 | 12.00 | 12.00 | 12.00 |
| Eumulgin ® B2 | 3.00 | 3.00 | 3.00 |
| Eutanol ® G | 2.00 | 2.00 | 2.00 |
| Cutina ® AGS | 2.00 | 2.00 | 2.00 |
| Cutina ® GMS-ES | 2.00 | 2.00 | 2.00 |
| XF42-B1989 | 1.50 | 1.50 | 1.50 |
| Potassium hydroxide 50% | 1.00 | 0.60 | 0.28 |
| Tetrasodium EDTA | 0.40 | 0.40 | 0.40 |
| Sodium sulfite | 0.10 | 0.10 | 0.08 |
| Ascorbic acid | 0.10 | 0.10 | 0.05 |
| Merquat Plus ® 3330 | 2.00 | 2.00 | 2.00 |
| Perfume | 0.50 | 0.50 | 0.50 |
| Ammonia (25% aqueous solution) | 6.00 | 6.00 | 6.00 |
| Aerosil ® 200 | 0.25 | 0.25 | 0.25 |
| p-Aminophenol | 0.070 | 0.035 | 0.024 |
| p-Phenylenediamine dihydrochloride | 0.780 | 0.510 | 0.220 |
| Resorcinol | 0.540 | 0.330 | 0.140 |
| m-Aminophenol | 0.085 | 0.029 | 0.011 |
| Water | to 100 | to 100 | to 100 |

Example 9

| Raw material | Quantity |
|---|---|
| Stearyl trimethyl ammonium chloride | 0.75 |
| Eumulgin ® B2 | 1.20 |
| Lanette ® O[10] | 4.00 |
| Propylene Glycol | 0.50 |
| Liquid Paraffin | 0.50 |
| Turpinal ® SL[11] | 0.20 |
| Sodium benzoate | 0.10 |
| Phenacetin | 0.10 |
| $Na_2HPO_4$ | 0.04 |
| Hydrogen peroxide (35% in water) | 17.00 |
| Water | to 100 |
| pH | 3.0 |

[10] $C_{16-18}$ fatty alcohol (INCI name: Cetearyl Alcohol) (Cognis)
[11] 1-hydroxyethane-1,1-diphosphonic acid (ca. 60% active substance content: INCI name: Etidronic Acid, Aqua (Water)) (Cognis)

Immediately before application, the coloring creams of Examples 1 to 3 and 5 to 8 were mixed with the oxidizing agent preparation of Example 9 in a ratio of 1:1. In the case of Example 4, a mixing ratio of coloring cream to oxidizing agent preparation of Example 9 of 1:2 was adjusted. The resulting preparations were each applied to a light brown, 50% gray normal hair tress. After a contact time of 30 mins. at 25° C., the tresses were rinsed with water, shampooed and dried with a blow dryer.

The colors obtained are shown in Table I. All the tresses were distinguished by their favorable wet and dry combability, were easy to disentangle and had a pleasant volume and high luster.

TABLE I

| Example | Color |
|---|---|
| 1 | Dark blond flat |
| 2 | Warm mid-brown |
| 3 | Extra light blond/beige |
| 4 | Ultra light blond/beige |
| 5 | Light blond/violet |
| 7 | Dark blond |
| 8 | Mid-blond |

Formulation Examples 10 to 16

| Raw material | 10 Quantity | 11 Quantity | 12 Quantity | 13 Quantity | 14 Quantity | 15 Quantity | 16 Quantity |
|---|---|---|---|---|---|---|---|
| Aqueous ammonium carbopol solution (1%) | 15.00 | 15.00 | 15.00 | 15.00 | 15.00 | 15.00 | 15.00 |
| Lanette ® E | 0.70 | 0.70 | 0.70 | 0.70 | 0.70 | 0.70 | 0.70 |
| Sodium lauryl ether sulfate (27% aqueous solution) | 4.40 | 4.40 | 4.40 | 4.40 | 4.40 | 4.40 | 4.40 |
| PEG 600 | 0.60 | 0.60 | 0.60 | 0.60 | 0.60 | 0.60 | 0.60 |
| Potassium oleate (12.5% aqueous solution) | 3.00 | 3.00 | 3.00 | 3.00 | 3.00 | 3.00 | 3.00 |
| Titanium dioxide | 0.15 | 0.15 | 0.15 | 0.15 | 0.15 | 0.15 | 0.15 |
| Cetylstearyl alcohol 50/50 | 12.00 | 12.00 | 12.00 | 12.00 | 12.00 | 12.00 | 12.00 |
| Eumulgin ® B2 | 3.00 | 3.00 | 3.00 | 3.00 | 3.00 | 3.00 | 3.00 |
| Eutanol ® G | 2.00 | 2.00 | 2.00 | 2.00 | 2.00 | 2.00 | 2.00 |
| Cutina ® AGS | 2.00 | 2.00 | 2.00 | 2.00 | 2.00 | 2.00 | 2.00 |
| Cutina ® GMS-SE | 1.00 | 1.00 | 1.00 | 1.00 | 1.00 | 1.00 | 2.00 |
| XF42-B1989 | 1.50 | 1.50 | 1.50 | 1.50 | 1.50 | 1.50 | 1.50 |
| Potassium hydroxide (50% in water) | 1.10 | 1.00 | 1.00 | 1.00 | 1.00 | 1.00 | 0.35 |
| Sodium carbonate, anhydrous | — | — | — | — | — | — | 1.00 |
| Diammonium hydrogen phosphate | — | — | — | — | — | — | 0.60 |
| Tetrasodium EDTA | 0.40 | 0.40 | 0.40 | 0.40 | 0.40 | 0.40 | 0.40 |
| Sodium sulfite | 0.40 | 0.40 | 0.40 | 0.40 | 0.40 | 0.40 | 0.40 |
| Ascorbic acid | 0.10 | 0.10 | 0.10 | 0.10 | 0.10 | 0.10 | 0.25 |
| Merquat Plus ® 3330 | 2.00 | 2.00 | 2.00 | 2.00 | 2.00 | 2.00 | 2.00 |
| Perfume | 0.50 | 0.50 | 0.50 | 0.50 | 0.50 | 0.50 | 0.10 |
| AMP-100 | — | — | 4.00 | 4.00 | — | 2.00 | — |
| Isopropanolamine | — | 8.00 | — | — | — | — | — |
| Ammonia (25% aqueous solution) | 6.00 | 2.25 | 6.00 | 6.00 | 6.00 | 6.00 | — |
| Aerosil ® 200 | 0.25 | 0.25 | 0.25 | 0.25 | 0.25 | 0.25 | 0.25 |
| Dye mixture of Table II | F1 | F2 | F3 | F4 | F5 | F6 | F7 |
| Water | to 100 | to 100 | to 100 | to 100 | to 100 | to 100 | to 100 |

TABLE II

Dye mixtures F1 to F7
The quantities in Table II are % by weight and are based on the weight of the coloring creams of corresponding Examples 10 to 16.

| Dye | F1 Quantity | F2 Quantity | F3 Quantity | F4 Quantity | F5 Quantity | F6 Quantity | F7 Quantity |
|---|---|---|---|---|---|---|---|
| p-Aminophenol | — | — | 0.18 | 0.18 | — | — | 0.30 |
| p-Phenylenediamine × 2 HCl | 0.78 | 0.86 | 0.90 | 0.80 | 0.85 | 0.85 | — |
| 4,4'-Diaminodiphenylamine sulfate | 0.02 | — | — | — | — | — | — |
| p-Toluylenediami9ne × $H_2OS_4$ | — | — | — | — | — | — | 0.30 |
| Resorcinol | 0.39 | 0.42 | 0.40 | 0.40 | 0.40 | 0.85 | 0.40 |
| m-Aminophenol | 0.10 | 0.05 | 0.49 | 0.40 | 0.13 | 0.10 | — |
| o-Aminophenol | — | — | 0.30 | 0.20 | 0.01 | 0.20 | — |
| 2,6-Diaminopyridine | 0.01 | — | — | — | — | — | — |
| 5-Amino-2-methylphenol | 0.02 | — | 0.10 | 0.10 | 0.04 | 0.04 | 0.03 |

TABLE II-continued

Dye mixtures F1 to F7
The quantities in Table II are % by weight and are based on the weight of the
coloring creams of corresponding Examples 10 to 16.

| Dye | F1 Quantity | F2 Quantity | F3 Quantity | F4 Quantity | F5 Quantity | F6 Quantity | F7 Quantity |
|---|---|---|---|---|---|---|---|
| m-Phenylenediamine | — | 0.01 | — | — | — | — | — |
| Imexine OAJ | — | — | 0.01 | 0.01 | — | — | — |
| 1,3-Diamino-4-nitrobenzene | — | — | — | — | — | — | 0.10 |
| 1,4-Diamino-2-nitrobenzene | — | — | — | — | 0.14 | 0.16 | — |
| 1,2-Diamino-4-nitrobenzene | — | — | 0.25 | 0.25 | — | — | 2.00 |

Formulation Examples 17 to 19

| Raw material | Example 17 Quantity | Example 18 Quantity | Example 19 Quantity |
|---|---|---|---|
| Aqueous ammonium carbopol solution (1%) | 15.00 | 15.00 | 15.00 |
| Lanette ® E | 0.70 | 0.70 | 0.70 |
| Sodium lauryl ether sulfate (27% aqueous solution) | 4.40 | 4.40 | 4.40 |
| PEG 600 | 0.60 | 0.60 | 0.60 |
| Potassium oleate (12.5% aqueous solution) | 3.00 | 3.00 | 3.00 |
| Titanium dioxide | 0.15 | 0.15 | 0.15 |
| Cetylstearyl alcohol 50/50 | 12.00 | 12.00 | 12.00 |
| Eumulgin ® B2 | 3.00 | 3.00 | 3.00 |
| Eutanol ® G | 2.00 | 2.00 | 2.00 |
| Cutina ® AGS | 2.00 | 2.00 | 2.00 |
| Cutina ® GMS-SE | 2.00 | 2.00 | 2.00 |
| XF42-B1989 | 1.50 | 1.50 | 1.50 |
| Potassium hydroxide (50% in water) | 0.29 | 1.00 | 0.25 |
| Sodium carbonate, anhydrous | — | — | — |
| Diammonium hydrogen phosphate | — | — | — |
| Tetrasodium EDTA | 0.40 | 0.40 | 0.40 |
| Sodium sulfite | 0.10 | 0.10 | 0.40 |
| Ascorbic acid | 0.05 | 0.05 | 0.25 |
| Merquat Plus ® 3330 | 2.00 | 2.00 | 2.00 |
| Perfume | 0.50 | 0.50 | 0.50 |
| AMP-100 | 7.80 | 5.00 | — |
| Monoethanolamine | — | — | 4.00 |
| Isopropanolamine | — | — | — |
| Ammonia (25% aqueous solution) | 7.30 | 6.00 | 5.60 |
| Aerosil ® 200 | 0.25 | 0.25 | 0.25 |
| Dye mixture of Table II | F8 | F9 | F10 |
| Water | to 100 | to 100 | to 100 |

Table III

Dye Mixtures F8 to F10

The quantities in Table III are % by weight and are based on the weight of the coloring creams of the corresponding Examples 17 to 19

| Dye | F8 Quantity | F9 Quantity | F10 Quantity |
|---|---|---|---|
| p-Aminophenol | — | 0.03 | 0.12 |
| p-Phenylenediamine × 2 HCl | — | 0.20 | 0.10 |
| p-Toluylenediamine × H$_2$SO$_4$ | 0.24 | — | — |
| Resorcinol | 0.03 | 0.15 | 0.40 |
| m-Aminophenol | 0.03 | 0.01 | — |
| 2,6-Diaminopyridine | 0.01 | — | — |
| 5-Amino-2-methylphenol | 0.03 | — | 0.05 |
| Imexine OAJ | 0.10 | — | — |
| 1,3-Diamino-4-nitrobenzene | — | — | 0.25 |

What is claimed is:

1. A two-component kit for coloring keratin fibers comprising a first preparation which contains dyes and/or dye precursors comprising: (A) at least one dialkyl polysiloxane or one of its derivatives and (B) an amphoteric polymer and a second preparation comprising at least one oxidizing agent and at least one quaternary ammonium compound selected from the group consisting of an alkyl trimethyl ammonium chloride, a dialkyl dimethyl ammonlum chloride, a trialkyl methyl ammonium chloride and combinations thereof.

2. The kit of claim 1 wherein component (A) is a dimethyl polysiloxane or one of its derivatives.

3. The kit of claim 1 wherein component (A) is an aminofunctional derivative of dialkyl polysiloxane.

4. The kit of claim 1 wherein component (A) is amodimethicone.

5. The kit of claim 1 wherein component (B) is a dimethyl diallyl ammonium salt and acrylic acid and/or methacrylic acid copolymer.

6. The kit of claim 5 wherein component (B) is a dimethyidiallyl ammonium chloride/acrylic acid/acrylamide terpolymer.

7. The kit of claim 1 wherein component (B) contains at least one monomer unit selected from esters or amides of acrylic acid and/or methacrylic acid.

8. The kit of claim 1 wherein the dye precursor contains at least one primary intermediate.

9. The kit of claim 1 wherein the dye precursor contains at least one indole and/or indoline derivative.

10. The kit of claim 1 further comprising at least one secondary intermediate.

11. The kit of claim 1 further comprising at least one substantive dye.

12. The kit of claim 1 wherein the quaternary ammonium compound is selected from the group consisting of cetyl trimethyl ammonlum chloride, stearyl trimethyl ammonium chloride, behenyl trimethyl ammonium chloride, distearyl dimethyl ammonium chloride, lauryl dimethyl ammonium chloride, lauryl dimethyl benzyl ammonium chloride and tricetyl methyl ammonium chloride.

13. The kit of claim 12 wherein the quaternary ammonium compound is stearyl trimethyl ammonium chloride.

14. A method for coloring keratin fibers comprising the steps of: (1) mixing the first and second preparations of claim 1; (2) contacting keratin fibers with the mixture formed in step 1; and, (3) after a contact time, rinsing the fibers thoroughly.

* * * * *